(12) United States Patent
Zipory et al.

(10) Patent No.: US 8,715,342 B2
(45) Date of Patent: May 6, 2014

(54) ANNULOPLASTY RING WITH INTRA-RING ANCHORING

(75) Inventors: Yuval Zipory, Modi'in (IL); Oz Cabiri, Macabim-Reut (IL); Yossi Gross, Moshav Mazor (IL)

(73) Assignee: Valtech Cardio, Ltd., Or Yehuda (IL)

( * ) Notice: Subject to any disclaimer, the term of this patent is extended or adjusted under 35 U.S.C. 154(b) by 623 days.

(21) Appl. No.: 12/437,103

(22) Filed: May 7, 2009

(65) Prior Publication Data

US 2010/0286767 A1 Nov. 11, 2010

(51) Int. Cl.
*A61F 2/24* (2006.01)

(52) U.S. Cl.
USPC .......................................... 623/2.11

(58) Field of Classification Search
USPC ..................... 623/2.11, 2.36–2.41
See application file for complete search history.

(56) References Cited

U.S. PATENT DOCUMENTS

| | | |
|---|---|---|
| 3,604,488 A | 9/1971 | Wishart et al. |
| 4,042,979 A | 8/1977 | Angell |
| 4,434,828 A | 3/1984 | Trincia |
| 4,602,911 A | 7/1986 | Ahmadi et al. |
| 4,625,727 A | 12/1986 | Leiboff |
| 4,778,468 A | 10/1988 | Rafiee |
| 4,917,698 A | 4/1990 | Carpenter et al. |
| 5,061,277 A | 10/1991 | Carpentier et al. |
| 5,104,407 A | 4/1992 | Lam et al. |
| 5,108,420 A | 4/1992 | Marks |
| 5,300,034 A | 4/1994 | Behnke et al. |
| 5,306,296 A | 4/1994 | Wright et al. |
| 5,450,860 A | 9/1995 | O'Connor |
| 5,477,856 A | 12/1995 | Lundquist |
| 5,669,919 A | 9/1997 | Sanders et al. |
| 5,674,279 A | 10/1997 | Wright et al. |
| 5,810,882 A | 9/1998 | Boldue |
| 5,843,120 A | 12/1998 | Israel et al. |

(Continued)

FOREIGN PATENT DOCUMENTS

| | | |
|---|---|---|
| WO | WO 92/05093 | 4/1992 |
| WO | WO 01/26586 | 4/2001 |

(Continued)

OTHER PUBLICATIONS

O'Reilly S et al., "Heart valve surgery pushes the envelope," Medtech Insight 8(3): 73, 99-108 (2006).

(Continued)

*Primary Examiner* — Thomas McEvoy
(74) *Attorney, Agent, or Firm* — Preti Flaherty Beliveau & Pachios LLP

(57) ABSTRACT

Apparatus is provided that includes an annuloplasty system for use on a subject. The system includes an annuloplasty ring, which includes a sleeve having a lumen, and at least one anchor, shaped so as to define a coupling head and a tissue coupling element, which tissue coupling element is shaped so as to define a longitudinal axis, and is configured to penetrate cardiac tissue of the subject in a direction parallel to the longitudinal axis. The system further includes an anchor deployment manipulator, configured to be removably positioned within the lumen of the sleeve, and, while so positioned, to deploy the tissue coupling element from a distal end of the deployment manipulator through a wall of the sleeve into the cardiac tissue in the direction parallel to the longitudinal axis of the tissue coupling element and parallel to a central longitudinal axis through the distal end of the deployment manipulator.

59 Claims, 15 Drawing Sheets

(56) References Cited

U.S. PATENT DOCUMENTS

| | | |
|---|---|---|
| 5,876,373 A | 3/1999 | Giba et al. |
| 5,961,440 A | 10/1999 | Schweich et al. |
| 5,961,539 A | 10/1999 | Northrup, III et al. |
| 6,045,497 A | 4/2000 | Schweich et al. |
| 6,050,936 A | 4/2000 | Schweich et al. |
| 6,059,715 A | 5/2000 | Schweich et al. |
| 6,165,119 A | 12/2000 | Schweich et al. |
| 6,251,092 B1 | 6/2001 | Qin et al. |
| 6,319,281 B1 | 11/2001 | Patel |
| 6,332,893 B1 | 12/2001 | Mortier et al. |
| 6,406,420 B1 | 6/2002 | McCarthy et al. |
| 6,451,054 B1 | 9/2002 | Stevens |
| 6,524,338 B1 | 2/2003 | Gundry |
| 6,537,314 B2 | 3/2003 | Langberg et al. |
| 6,564,805 B2 | 5/2003 | Garrison et al. |
| 6,569,198 B1 | 5/2003 | Wilson et al. |
| 6,579,297 B2 | 6/2003 | Bicek et al. |
| 6,589,160 B2 | 7/2003 | Schweich et al. |
| 6,602,288 B1 | 8/2003 | Cosgrove |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,629,921 B1 | 10/2003 | Schweich et al. |
| 6,651,671 B1 | 11/2003 | Donlon et al. |
| 6,682,558 B2 | 1/2004 | Tu et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,709,456 B2 | 3/2004 | Langberg et al. |
| 6,718,985 B2 | 4/2004 | Hlavka et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,510 B2 | 7/2004 | Vidlund et al. |
| 6,786,924 B2 | 9/2004 | Ryan et al. |
| 6,802,319 B2 | 10/2004 | Stevens et al. |
| 6,805,710 B2 | 10/2004 | Bolling et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,482 B2 | 6/2005 | McCarthy et al. |
| 6,960,217 B2 | 11/2005 | Bolduc |
| 6,986,775 B2 | 1/2006 | Morales et al. |
| 6,989,028 B2 | 1/2006 | Lashinski et al. |
| 7,004,176 B2 | 2/2006 | Lau |
| 7,011,669 B2 | 3/2006 | Kimblad |
| 7,011,682 B2 | 3/2006 | Lashinski et al. |
| 7,037,334 B1 | 5/2006 | Hlavka et al. |
| 7,087,064 B1 | 8/2006 | Hyde |
| 7,101,395 B2 | 9/2006 | Tremulis et al. |
| 7,112,207 B2 | 9/2006 | Allen et al. |
| 7,125,421 B2 | 10/2006 | Tremulis et al. |
| 7,159,593 B2 | 1/2007 | McCarthy |
| 7,169,187 B2 | 1/2007 | Datta et al. |
| 7,175,660 B2 | 2/2007 | Cartledge et al. |
| 7,186,262 B2 | 3/2007 | Saadat |
| 7,189,199 B2 | 3/2007 | McCarthy et al. |
| 7,226,467 B2 | 6/2007 | Lucatero et al. |
| 7,238,191 B2 | 7/2007 | Bachmann |
| 7,294,148 B2 | 11/2007 | McCarthy |
| 7,297,150 B2 | 11/2007 | Cartledge et al. |
| 7,311,728 B2 | 12/2007 | Solem et al. |
| 7,316,710 B1 | 1/2008 | Cheng et al. |
| 7,329,280 B2 | 2/2008 | Bolling et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,452,376 B2 | 11/2008 | Lim et al. |
| 7,455,690 B2 | 11/2008 | Cartledge et al. |
| 7,507,252 B2 | 3/2009 | Lashinski et al. |
| 7,530,995 B2 | 5/2009 | Quijano |
| 7,549,983 B2 | 6/2009 | Roue et al. |
| 7,563,267 B2 | 7/2009 | Goldfarb et al. |
| 7,563,273 B2 | 7/2009 | Goldfarb et al. |
| 7,588,582 B2 | 9/2009 | Starksen et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,753,924 B2 | 7/2010 | Starksen et al. |
| 7,927,370 B2 | 4/2011 | Webler et al. |
| 7,993,368 B2 | 8/2011 | Gambale et al. |
| 8,012,201 B2 | 9/2011 | Lashinski et al. |
| 8,070,804 B2 | 12/2011 | Hyde |
| 8,142,495 B2 | 3/2012 | Hasenkam |
| 8,287,591 B2 | 10/2012 | Keidar |
| 2002/0087048 A1 | 7/2002 | Brock et al. |
| 2002/0103532 A1 | 8/2002 | Langberg et al. |
| 2002/0151961 A1 | 10/2002 | Lashinski |
| 2002/0173841 A1 | 11/2002 | Ortiz et al. |
| 2002/0177904 A1 | 11/2002 | Huxel et al. |
| 2003/0050693 A1 | 3/2003 | Quijano et al. |
| 2003/0105519 A1 | 6/2003 | Fasol et al. |
| 2003/0167062 A1 | 9/2003 | Gambale et al. |
| 2003/0233142 A1 | 12/2003 | Morales et al. |
| 2004/0019377 A1 | 1/2004 | Taylor et al. |
| 2004/0024451 A1 | 2/2004 | Johnson et al. |
| 2004/0049207 A1 | 3/2004 | Goldfarb et al. |
| 2004/0092962 A1 | 5/2004 | Thornton et al. |
| 2004/0122514 A1 | 6/2004 | Fogarty et al. |
| 2004/0148021 A1 | 7/2004 | Cartledge et al. |
| 2004/0153146 A1* | 8/2004 | Lashinski et al. ............ 623/2.36 |
| 2004/0181287 A1 | 9/2004 | Gellman |
| 2004/0186566 A1 | 9/2004 | Hindrichs |
| 2004/0236419 A1 | 11/2004 | Milo |
| 2005/0004668 A1 | 1/2005 | Aklog et al. |
| 2005/0016560 A1 | 1/2005 | Voughlohn |
| 2005/0055087 A1 | 3/2005 | Starksen |
| 2005/0060030 A1 | 3/2005 | Lashinski |
| 2005/0090827 A1 | 4/2005 | Gedebou |
| 2005/0171601 A1 | 8/2005 | Cosgrove et al. |
| 2005/0177228 A1 | 8/2005 | Solem et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0288781 A1 | 12/2005 | Moaddeb et al. |
| 2006/0020326 A9 | 1/2006 | Bolduc et al. |
| 2006/0025787 A1 | 2/2006 | Morales et al. |
| 2006/0041319 A1 | 2/2006 | Taylor et al. |
| 2006/0069429 A1 | 3/2006 | Spence et al. |
| 2006/0129166 A1 | 6/2006 | Lavelle |
| 2006/0161265 A1 | 7/2006 | Levine et al. |
| 2006/0241656 A1 | 10/2006 | Starksen et al. |
| 2006/0241748 A1 | 10/2006 | Lee et al. |
| 2006/0282161 A1 | 12/2006 | Huynh et al. |
| 2006/0287716 A1 | 12/2006 | Banbury et al. |
| 2007/0016287 A1 | 1/2007 | Cartledge |
| 2007/0027536 A1 | 2/2007 | Mihaljevic et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0080188 A1 | 4/2007 | Spence et al. |
| 2007/0112422 A1 | 5/2007 | Dehdashtian |
| 2007/0118151 A1 | 5/2007 | Davidson |
| 2007/0162111 A1 | 7/2007 | Fukamachi et al. |
| 2007/0198082 A1 | 8/2007 | Kapadia et al. |
| 2007/0213582 A1 | 9/2007 | Zollinger et al. |
| 2007/0219558 A1 | 9/2007 | Deutsch |
| 2007/0250160 A1 | 10/2007 | Rafiee |
| 2007/0255400 A1 | 11/2007 | Parravicini et al. |

(56) References Cited

U.S. PATENT DOCUMENTS

| | | |
|---|---|---|
| 2007/0282375 A1 | 12/2007 | Hindrichs et al. |
| 2007/0295172 A1 | 12/2007 | Swartz |
| 2008/0004697 A1 | 1/2008 | Lichtenstein et al. |
| 2008/0027483 A1 | 1/2008 | Cartledge |
| 2008/0035160 A1 | 2/2008 | Woodson et al. |
| 2008/0058595 A1 | 3/2008 | Snoke et al. |
| 2008/0086203 A1 | 4/2008 | Roberts |
| 2008/0097523 A1 | 4/2008 | Bolduc et al. |
| 2008/0177382 A1 | 7/2008 | Hyde et al. |
| 2008/0195126 A1 | 8/2008 | Solem |
| 2008/0262609 A1 | 10/2008 | Gross |
| 2008/0288044 A1 | 11/2008 | Osborne |
| 2009/0043153 A1 | 2/2009 | Zollinger et al. |
| 2009/0054969 A1 | 2/2009 | Salahieh et al. |
| 2009/0099650 A1 | 4/2009 | Bolduc et al. |
| 2009/0171439 A1 | 7/2009 | Nissl |
| 2009/0177266 A1 | 7/2009 | Powell et al. |
| 2009/0326648 A1 | 12/2009 | Machold et al. |
| 2010/0130992 A1 | 5/2010 | Machold et al. |
| 2010/0161041 A1 | 6/2010 | Maisano et al. |
| 2010/0161043 A1 | 6/2010 | Maisano |
| 2010/0161047 A1 | 6/2010 | Cabiri |
| 2010/0168845 A1 | 7/2010 | Wright |
| 2010/0174358 A1 | 7/2010 | Rabkin et al. |
| 2010/0179574 A1 | 7/2010 | Longoria |
| 2010/0234935 A1 | 9/2010 | Bashiri et al. |
| 2010/0280604 A1 | 11/2010 | Zipory et al. |
| 2010/0324598 A1 | 12/2010 | Anderson |
| 2011/0029066 A1 | 2/2011 | Gilad |
| 2011/0093002 A1 | 4/2011 | Rucker et al. |
| 2011/0184510 A1 | 7/2011 | Maisano et al. |

FOREIGN PATENT DOCUMENTS

| | | |
|---|---|---|
| WO | WO 02/085251 | 10/2002 |
| WO | WO 02/085252 | 10/2002 |
| WO | WO 2005/021063 | 3/2005 |
| WO | WO 2006/097931 | 3/2006 |
| WO | WO 2006/116558 | 11/2006 |
| WO | WO 2007/136783 | 11/2007 |
| WO | WO 2008/068756 | 6/2008 |
| WO | WO 2010/073246 | 7/2010 |
| WO | WO 2011/089601 | 7/2011 |

OTHER PUBLICATIONS

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Swain CP et al., "An endoscopically deliverable tissue-transfixing device for securing biosensors in the gastrointestinal tract," Gastrointestinal Endoscopy 40(6): 730-734 (1994).
Odell JA et al., "Early Results of a Simplified Method of Mitral Valve Annuloplasty," Circulation 92:150-154 (1995).
An International Search Report dated Sep. 8, 2009, which issued during the prosecution of Applicant's PCT/IL09/00593.
U.S. Appl. No. 60/873,075, filed Dec. 5, 2006.
U.S. Appl. No. 60/902,146, filed Feb. 16, 2007.
U.S. Appl. No. 61/001,013, filed Oct. 29, 2007.
U.S. Appl. No. 61/132,295, filed Jun. 16, 2008.
"Two dimensional real-time ultrasonic imaging of the heart and great vessels", Mayo Clin Proc. vol. 53:271-303, 1978.
An International Search Report dated Jun. 10, 2010, which issued during the prosecution of Applicant's PCT/IL09/01209.
An Office Action dated Apr. 6, 2010, which issued during the prosecution of Applicant's U.S. Appl. No. 12/484,512.
An Office Action dated Oct. 6, 2010, which issued during the prosecution of Applicant's U.S. Appl. No. 12/484,512.
An International Search Report and a Written Opinion, both dated Nov. 8, 2010, issued during the prosecution of Applicant's PCT/IL10/00358.
An Office Action dated Aug. 4, 2010, which issued during the prosecution of Applicant's U.S. Appl. No. 12/341,960.
An Office Action dated Mar. 9, 2012, which issued during the prosecution of U.S. Appl. No. 12/689,635.
An Office Action dated Jan. 23, 2012, which issued during the prosecution of U.S. Appl. No. 12/692,061.
An Office Action dated Dec. 29, 2011, which issued during the prosecution of U.S. Appl. No. 12/563,952.
An International Search Report dated Aug. 17, 2010, which issued during the prosecution of Applicant's PCT/IL2010/000357.
An International Preliminary Report on Patentability dated Nov. 9, 2011, which issued during the prosecution of Applicant's PCT/IL2010/000357.
An International Search Report dated Feb. 2, 2012, which issued during the prosecution of Applicant's PCT/IL2011/000600.
An International Search Report dated Jun. 10, 2010, which issued during the prosecution of Applicant's PCT/IL2009/001209.
An office action dated Oct. 9, 2013, which issued during the prosecution of U.S. Appl. No. 12/996,954.
An Office Action dated May 6, 2013, which issued during the prosecution of U.S. Appl. No. 12/689,693.
Office action dated Jul. 20, 2012, which issued during the prosecution of U.S. Appl. No. 12/843,312.
An Office Action dated Nov. 30, 2012, which issued during the prosecution of U.S. Appl. No. 12/689,635.
An International Search Report and a Written Opinion both dated Dec. 6, 2012, which issued during the prosecution of Applicant's PCT/IL2012/000250.
An Office Action dated Apr. 1, 2013, which issued during the prosecution of U.S. Appl. No. 13/167,476.
Supplementary European Search Report dated Mar. 28, 2013, which issued during the prosecution of EP Patent Application No. 10772091.
Office Action dated Jul. 20, 2012, which issued during the prosecution of U.S. Appl. No. 12/843,412.
An Office Action dated Jun. 7, 2013, which issued during the prosecution of U.S. Appl. No. 13/141,606.
Office Action dated Feb. 3, 2014 in U.S. Appl. No. 12/689,693.
Office Action dated Dec. 16, 2013 in U.S. Appl. No. 13/666,262.
Office Action dated Nov. 21, 2013 in U.S. Appl. No. 13/167,476.
Office Action dated Dec. 19, 2013 in U.S. Appl. No. 14/027,934.

* cited by examiner

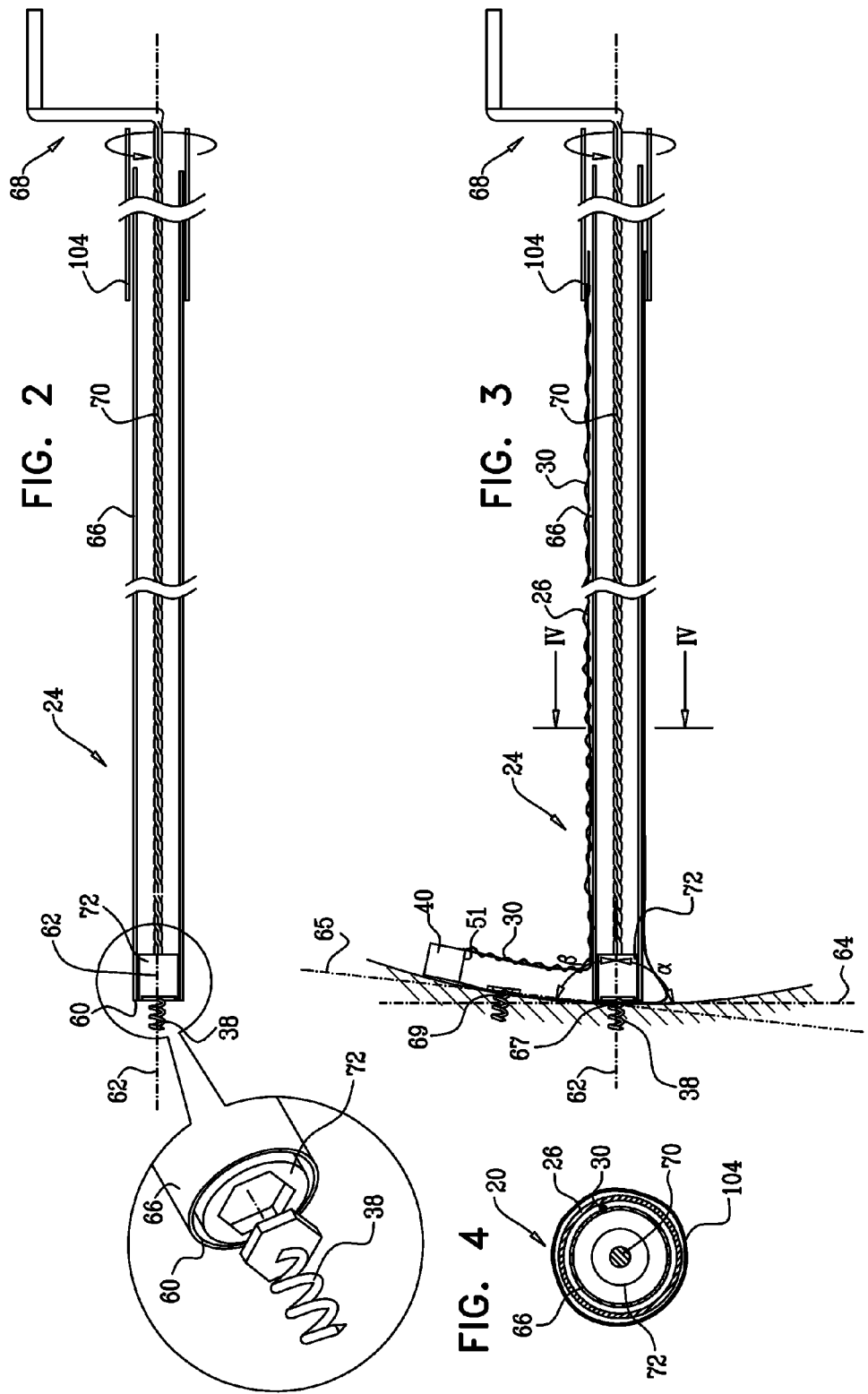

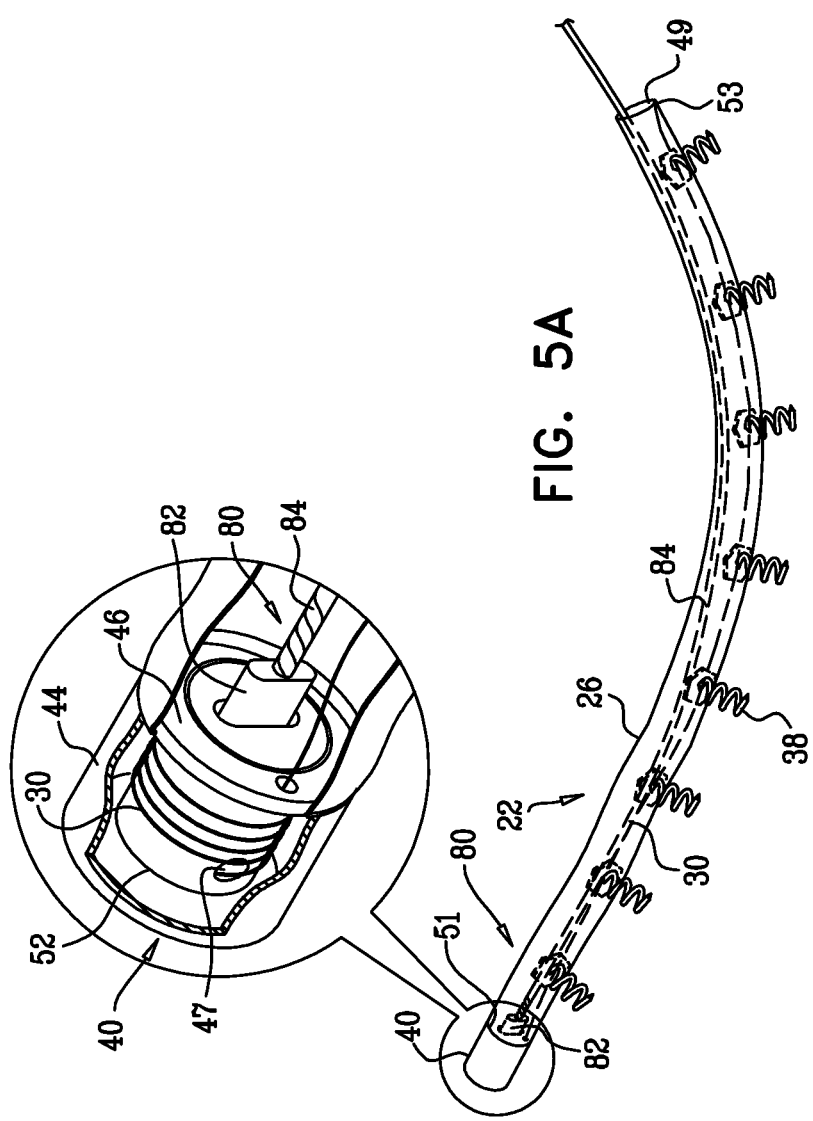

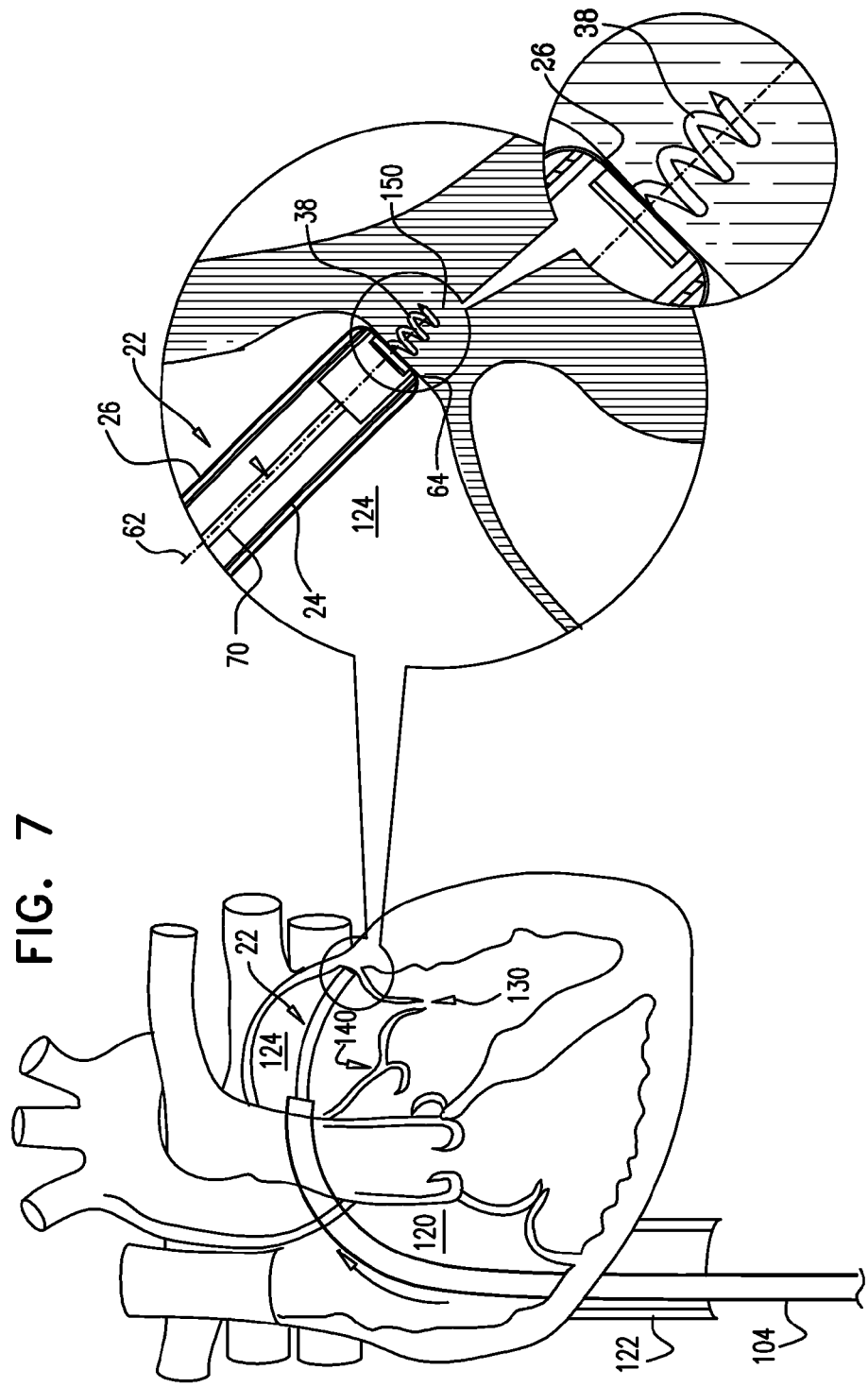

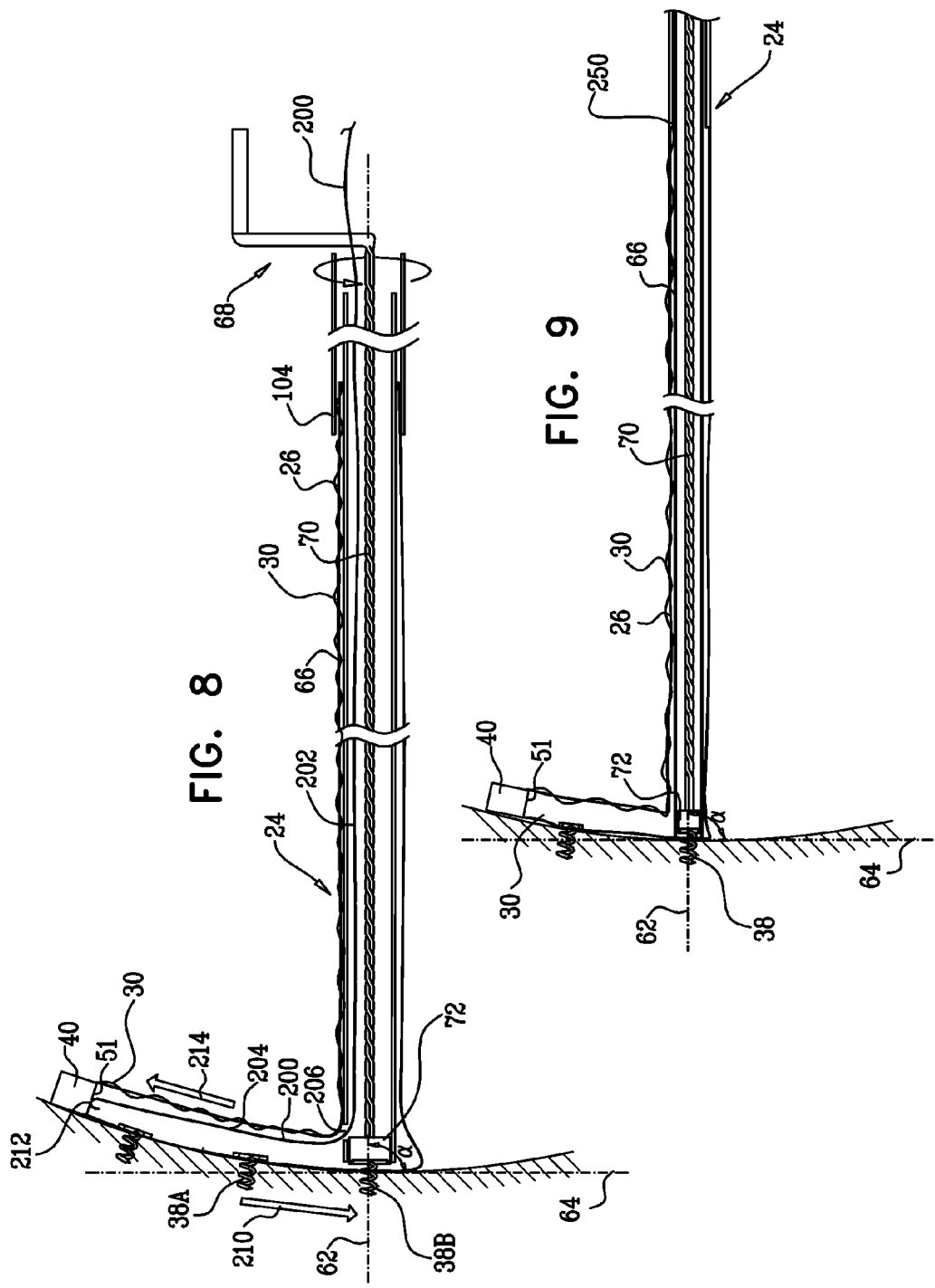

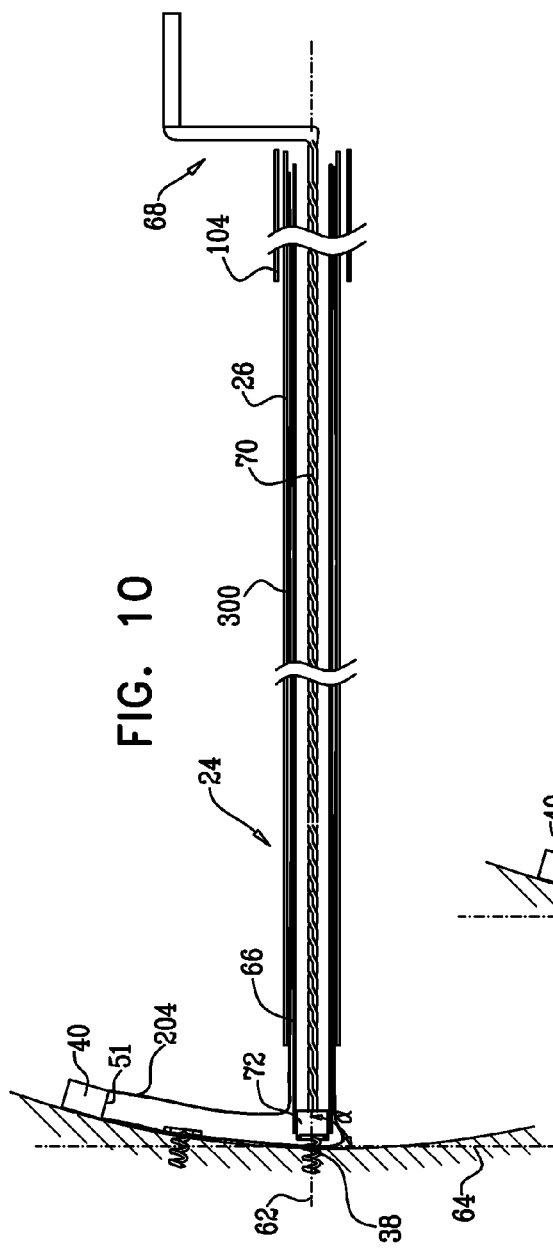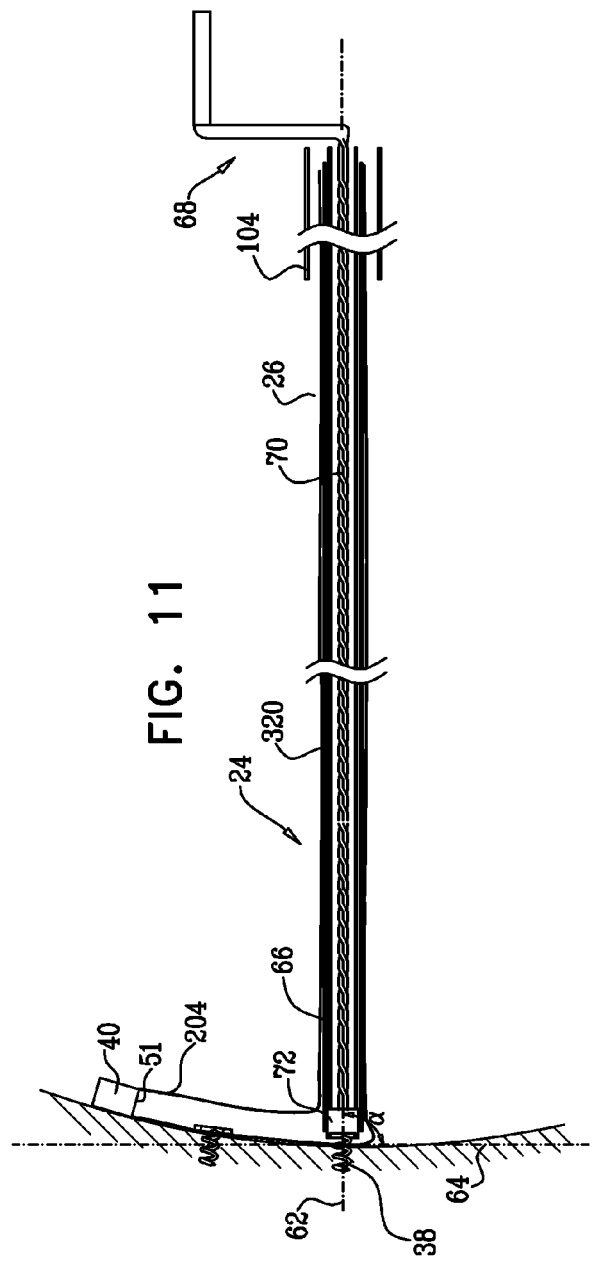

ANNULOPLASTY RING WITH INTRA-RING ANCHORING

FILED OF THE INVENTION

The present invention relates in general to valve repair, and more specifically to repair of an atrioventricular valve of a patient.

BACKGROUND OF THE INVENTION

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

US Patent Application Publication 2007/0055206 to To et al., which is incorporated herein by reference, describes devices, methods, and kits for deployment of tissue anchors. In some variations, the devices comprise a shaft defining a lumen for housing at least one anchor therein (the anchor having an eyelet) and a mechanism for deploying the anchor distally from the lumen, wherein the inner diameter of the lumen is the same size or smaller than the diameter of the eyelet of the anchor to be disposed therein when the anchor is in an expanded configuration. In some variations, the methods comprise loading an anchor within a lumen of a shaft (where the anchor comprises an eyelet and the shaft has a slot therethrough), passing a linking member through the slot and through the eyelet of the anchor, and deploying the anchor. Other methods comprise loading an anchor within a lumen of a shaft, and deploying the anchor distally from the lumen.

US Patent Application Publication 2007/0080188 to Spence et al., which is incorporated herein by reference, describes systems and methods for securing tissue including the annulus of a mitral valve. The systems and methods may employ catheter based techniques and devices to plicate tissue and perform an annuloplasty. Magnets may be used for guidance in deploying fasteners from a catheter. The fasteners are cinched with a flexible tensile member.

U.S. Pat. No. 6,619,291 to Hlavka et al., which is incorporated herein by reference, describes a minimally invasive method of performing annuloplasty. A method for performing a procedure on a mitral valve of a heart includes inserting an implant into a left ventricle and orienting the implant in the left ventricle substantially below the mitral valve. The implant and tissue around the mitral valve are connected and tension is provided to the implant, in one embodiment, in order to substantially reduce an arc length associated with the mitral valve. In another embodiment, the implant is inserted into the left ventricle through the aorta and the aortic valve.

US Patent Application Publication 2006/0241656 to Starksen et al., which is incorporated herein by reference, describes devices, systems and methods for facilitating positioning of a cardiac valve annulus treatment device, thus enhancing treatment of the annulus. Methods generally involve advancing an anchor delivery device through vasculature of the patient to a location in the heart for treating the valve annulus, contacting the anchor delivery device with a length of the valve annulus, delivering a plurality of coupled anchors from the anchor delivery device to secure the anchors to the annulus, and drawing the anchors together to circumferentially tighten the valve annulus. Devices generally include an elongate catheter having at least one tensioning member and at least one tensioning actuator for deforming a distal portion of the catheter to help it conform to a valve annulus. The catheter device may be used to navigate a subannular space below a mitral valve to facilitate positioning of an anchor delivery device.

US Patent Application Publication 2007/0051377 to Douk et al., which is incorporated herein by reference, describes a catheter-based, annulus reduction device and system for cardiac valve repair and method of using the same. The system is usable for treating mitral valve regurgitation and comprises a catheter, a reduction ring carried within the catheter, the reduction ring including a plurality of exit ports formed in a side wall of the reduction ring and filament received in the reduction ring. The filament includes a plurality of radially extendible barbs corresponding to the sidewall openings. The reduction ring carrying the filament is deployed adjacent a mitral valve annulus and the filament is translated relative to the reduction ring to deploy the barbs through the exit ports and into the annulus and to further translate the reduction ring with deployed barbs to reshape the annulus.

US Patent Application Publication 2006/0025787 to Morales et al., which is incorporated herein by reference, describes methods and devices that provide constriction of a heart valve annulus to treat cardiac valve regurgitation and other conditions. Embodiments typically include a device for attaching a cinching or tightening apparatus to a heart valve annulus to reduce the circumference of the annulus, thus reducing valve regurgitation. Tightening devices may include multiple tethered clips, multiple untethered crimping clips, stabilizing devices, visualization devices, and the like. In one embodiment, a plurality of tethered clips is secured circumferentially to a valve annulus, and the tether coupling the clips is cinched to reduce the circumference of at least a portion of the annulus. Methods and devices may be used in open heart surgical procedures, minimally invasive procedures, catheter-based procedures, and/or procedures on beating hearts or stopped hearts.

U.S. Pat. No. 7,431,692 to Zollinger et al., which is incorporated herein by reference, describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US Patent Application Publication 2007/0016287 to Cartledge et al., which is incorporated herein by reference, describes an implantable device for controlling shape and/or size of an anatomical structure or lumen. The implantable device has an adjustable member configured to adjust the dimensions of the implantable device. The implantable device is housed in a catheter and insertable from a minimally invasive surgical entry. An adjustment tool actuates the adjustable member and provide for adjustment before, during or after the anatomical structure or lumen resumes near normal to normal physiologic function.

US Patent Application Publication 2004/0236419 to Milo, which is incorporated herein by reference, describes methods for reconfiguring an atrioventricular heart valve that may use systems comprising a partial or complete annuloplasty rings proportioned to reconfigure a heart valve that has become in some way incompetent, a pair of trigonal sutures or implantable anchors, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. Annuloplasty rings may be complete or partial and may be fenestrated. One alternative method routes a flexible wire, preferably of shape-memory material, through the bights of pre-implanted staples. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various ones of these systems are described as being implanted non-invasively using a delivery catheter.

US Patent Application Publication 2005/0171601 to Cosgrove et al., which is incorporated herein by reference, describes an annuloplasty repair segment and template for heart valve annulus repair. The elongate flexible template may form a distal part of a holder that also has a proximal handle. Alternatively, the template may be releasably attached to a mandrel that slides within a delivery sheath, the template being released from the end of the sheath to enable manipulation by a surgeon. A tether connecting the template and mandrel may also be provided. The template may be elastic, temperature responsive, or multiple linked segments. The template may be aligned with the handle and form a two- or three-dimensional curve out of alignment with the handle such that the annuloplasty repair segment attached thereto conforms to the curve. The template may be actively or passively converted between its straight and curved positions. The combined holder and ring is especially suited for minimally-invasive surgeries in which the combination is delivered to an implantation site through a small access incision with or without a cannula, or through a catheter passed though the patient's vasculature.

The following patents and patent application publications, all of which are incorporated herein by reference, may be of interest:

U.S. Pat. No. 5,306,296 to Wright et al.
U.S. Pat. No. 5,674,279 to Wright et al.
U.S. Pat. No. 5,961,539 to Northrup, III et al.
U.S. Pat. No. 6,524,338 to Gundry
U.S. Pat. No. 6,569,198 to Wilson et al.
U.S. Pat. No. 6,602,288 to Cosgrove et al.
U.S. Pat. No. 6,602,289 to Colvin et al.
U.S. Pat. No. 6,689,164 to Seguin
U.S. Pat. No. 6,702,826 to Liddicoat et al.
U.S. Pat. No. 6,718,985 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
U.S. Pat. No. 7,186,262 to Saadat
US Patent Application Publication 2002/0087048 to Brock et al.
US Patent Application Publication 2002/0173841 to Ortiz et al.
US Patent Application Publication 2003/0050693 to Quijano et al.
US Patent Application Publication 2003/0167062 to Gambale et al.
US Patent Application Publication 2004/0024451 to Johnson et al.
US Patent Application Publication 2004/0148021 to Cartledge et al.
US Patent Application Publication 2005/0055087 to Starksen
US Patent Application Publication 2005/0288781 to Moaddeb et al.
US Patent Application Publication 2006/0069429 to Spence et al.
PCT Publication WO 01/26586 to Seguin
PCT Publication WO 02/085251 to Hlavka et al.
PCT Publication WO 02/085252 to Hlavka et al.
PCT Publication WO 07/136783 to Cartledge et al.

The following articles, all of which are incorporated herein by reference, may be of interest:

O'Reilly S et al., "Heart valve surgery pushes the envelope," Medtech Insight 8(3): 73, 99-108 (2006)

Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

Swain C P et al., "An endoscopically deliverable tissue-transfixing device for securing biosensors in the gastrointestinal tract," Gastrointestinal Endoscopy 40(6): 730-734 (1994)

Odell J A et al., "Early Results of a Simplified Method of Mitral Valve Annuloplasty," Circulation 92:150-154 (1995)

SUMMARY OF THE INVENTION

In some embodiments of the present invention, an adjustable partial annuloplasty ring is provided for repairing a dilated valve annulus of an atrioventricular valve, such as a mitral valve. The annuloplasty ring comprises a flexible sleeve and a plurality of anchors. An anchor deployment manipulator is advanced into a lumen of the sleeve, and, from within the lumen, deploys the anchors through a wall of the sleeve and into cardiac tissue, thereby anchoring the sleeve around a portion of the valve annulus. The anchors are typically deployed from a distal end of the manipulator while the distal end is positioned such that a central longitudinal axis through the distal end of the manipulator forms an angle with a surface of the cardiac tissue of between about 45 and 90 degrees, e.g., between about 75 and 90 degrees, such as about 90 degrees. Typically, the anchors are deployed from the distal end of the manipulator into the cardiac tissue in a direction parallel to the central longitudinal axis through the distal end of the manipulator.

In some embodiments of the present invention, the anchors are deployed from the left atrium into the upper region of the ventricular wall near the atrium, tissue of which generally provides more secure anchoring than does the atrial wall. The above-mentioned angle of deployment enables such deployment into the upper region of the ventricular wall.

In some embodiments of the present invention, the anchor deployment manipulator comprises a steerable outer tube in which is positioned an anchor driver having an elongated, flexible shaft. Rotation of the anchor driver screws the anchors into the cardiac tissue. The anchors may, for example, be helical in shape. For some applications, the plurality of anchors are applied using the manipulator by loading a first one of the anchors onto the anchor driver, and deploying the anchor into the cardiac tissue. The anchor driver is withdrawn from the body of the subject, and a second one of the anchors is loaded onto the anchor driver. The anchor driver is reintroduced into the sleeve of the annuloplasty ring, and the second anchor is deployed. These steps are repeated until all of the anchors have been deployed. Alternatively, the anchor driver is configured to simultaneously hold a plurality of anchors, and to deploy them one at a time.

Typically, the manipulator is gradually withdrawn in a proximal direction during the anchoring procedure as anchors are deployed. The first anchor is thus deployed most distally in the sleeve (generally at or within a few millimeters of the distal tip of the sleeve), and each subsequent anchor is deployed more proximally.

The annuloplasty ring is typically configured to be placed only partially around the valve annulus (i.e., to assume a C-shape), and, once anchored in place, to be contracted so as to circumferentially tighten the valve annulus. To this end, the annuloplasty ring comprises a flexible contracting member such as a wire, which is typically positioned within the lumen of the sleeve. The annuloplasty ring further comprises a contracting mechanism which facilitates contracting of the annuloplasty ring. For some applications, the contracting mechanism comprises a spool to which a first end of the contracting member is coupled. The spool is positioned in a vicinity of either the proximal or the distal end of the sleeve. A second end of the contracting member is coupled to the sleeve in a vicinity of the end of the sleeve opposite the end to which the spool is positioned. Rotation of the spool winds a portion of the contracting member around the spool, thereby pulling the far end of the ring toward the spool and tightening the ring. For some applications, the spool is positioned in a vicinity of the distal end of the sleeve, and is oriented such that a driving interface thereof is accessible from within the sleeve. A screwdriver tool is inserted into the sleeve, and used to rotate the spool via the driving interface of the spool.

All of the tools and elements of the annuloplasty system that are introduced into left atrium are contained within the sleeve of the annuloplasty ring, which reduces the risk that any elements of the system will accidentally be released to the blood circulation, or damage surrounding tissue. In addition, the lumen of the sleeve provides guidance if it should be necessary to return to a previously deployed anchor, such as to tighten, loosen, remove, or relocate the anchor. For some applications, the anchors comprise helical screws, which facilitate such adjusting or removing.

The annuloplasty ring may be advanced toward the annulus of a valve in any suitable procedure, e.g., a transcatheter procedure, a minimally invasive procedure, or an open heart procedure.

There is therefore provided, in accordance with an embodiment of the present invention, apparatus including an annuloplasty system for use on a subject, which includes:

an annuloplasty ring, which includes a sleeve having a lumen;

at least one anchor, shaped so as to define a coupling head and a tissue coupling element, which tissue coupling element is shaped so as to define a longitudinal axis, and is configured to penetrate cardiac tissue of the subject in a direction parallel to the longitudinal axis; and an anchor deployment manipulator, configured to be removably positioned within the lumen of the sleeve, and, while so positioned, to deploy the tissue coupling element from a distal end of the deployment manipulator through a wall of the sleeve into the cardiac tissue in the direction parallel to the longitudinal axis of the tissue coupling element and parallel to a central longitudinal axis of the deployment manipulator through the distal end of the deployment manipulator.

Typically, the annuloplasty ring includes a partial annuloplasty ring.

For some applications, the coupling element is shaped so as to define a shape selected from the group consisting of: a helix, a spiral, and a screw shaft.

In an embodiment, the annuloplasty ring includes a spool coupled to the sleeve, and a flexible contracting member that is coupled to the spool and the sleeve, such that winding the contracting member around the spool tightens the ring.

In an embodiment, the deployment manipulator includes steering functionality. For some applications, the deployment manipulator includes a tube, which is configured to provide the steering functionality; and an anchor driver, which includes an elongated, flexible shaft which is at least partially positioned within the tube.

In an embodiment, the deployment manipulator is configured to deploy the at least one anchor from the distal end of the deployment manipulator through the wall of the sleeve into the cardiac tissue, while the distal end of the deployment manipulator is positioned such that the central longitudinal axis through the distal end of the deployment manipulator forms an angle of between 45 and 90 degrees with the wall of the sleeve at a point at which the anchor penetrates the wall. For some applications, the point on the wall is a first point on the wall, and the angle is a first angle, the at least one anchor is a first anchor of a plurality of anchors that also includes a second anchor most recently deployed before the first anchor through a second point on the wall, and the deployment manipulator is configured to deploy the first anchor while the distal end of the deployment manipulator is positioned such that the central longitudinal axis forms a second angle of between 45 and 90 degrees with a line defined by the first point and the second point.

For some applications, the apparatus further includes a pusher element which is positioned within the sleeve, and which is configured to, upon being pushed distally, move the distal end of the deployment manipulator proximally within the sleeve by engaging an interior surface of the sleeve.

There is further provided, in accordance with an embodiment of the present invention, a method including:

positioning an anchor deployment manipulator at least partially within a lumen of a sleeve of an annuloplasty ring;

placing, into an atrium of a subject in a vicinity of an annulus of an atrioventricular valve, at least a portion of the sleeve that contains a distal end of the deployment manipulator; and deploying at least one anchor from the distal end of the deployment manipulator through a wall of the sleeve such that a coupling element of the anchor enters cardiac tissue of the subject in a direction parallel to a central longitudinal axis of the deployment manipulator through the distal end of the deployment manipulator.

In an embodiment, deploying includes deploying the at least one anchor from the distal end of the deployment manipulator through the wall of the sleeve into the cardiac tissue, while the distal end of the deployment manipulator is positioned such that the central longitudinal axis of the deployment manipulator through the distal end of the deployment manipulator forms an angle of between 45 and 90 degrees with the wall of the sleeve at a point at which the anchor penetrates the wall. For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

Typically, the annuloplasty ring includes a partial annuloplasty ring, and positioning the deployment manipulator includes positioning the deployment manipulator within the lumen of the partial annuloplasty ring.

In an embodiment, the deployment manipulator includes steering functionality, and placing the sleeve includes steering the deployment manipulator using the steering functionality.

For some applications, deploying the anchor includes deploying the anchor from the atrium into an upper region of a ventricular wall near the atrium.

For some applications, the method further includes positioning a pusher element at least partially within the lumen of the sleeve of the annuloplasty ring; and moving the distal end of the deployment manipulator proximally within the sleeve by pushing the pusher element distally such that the pusher element engages an interior surface of the sleeve.

In an embodiment, the method further includes tightening the annuloplasty ring by winding a flexible contracting member of the ring around a spool coupled to the ring.

There is still further provided, in accordance with an embodiment of the present invention, apparatus including an annuloplasty system for use on a subject, which includes:

an annuloplasty ring, which includes a sleeve having a lumen;

at least one anchor; and an anchor deployment manipulator, configured to be removably positioned within the lumen of the sleeve, and, while so positioned, to deploy the at least one anchor from a distal end of the deployment manipulator through a wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

Typically, the annuloplasty ring includes a partial annuloplasty ring.

In an embodiment, the deployment manipulator includes steering functionality.

For some applications, the point on the wall is a first point on the wall, and the angle is a first angle, the at least one anchor is a first anchor of a plurality of anchors that also includes a second anchor most recently deployed before the first anchor through a second point on the wall, and the anchor deployment manipulator is configured to deploy the first anchor while the distal end of the deployment manipulator is positioned such that the central longitudinal axis forms a second angle of between 45 and 90 degrees with a line defined by the first point and the second point.

For some applications, the anchor is shaped so as to define a coupling head and a tissue coupling element, which tissue coupling element is shaped so as to define a longitudinal axis, and is configured to penetrate cardiac tissue of the subject in a direction parallel to the longitudinal axis, and the anchor deployment manipulator is configured to deploy the anchor from the distal end of the deployment manipulator such that the coupling element enters the cardiac tissue in a direction parallel to the central longitudinal axis of the deployment manipulator through the distal end of the deployment manipulator.

For some applications, the anchor is shaped so as to define a coupling head and a tissue coupling element, which is shaped so as to define a shape selected from the group consisting of: a helix, a spiral, and a screw shaft.

There is additionally provided, in accordance with an embodiment of the present invention, a method including:

positioning an anchor deployment manipulator at least partially within a lumen of a sleeve of an annuloplasty ring;

placing, into an atrium of a subject in a vicinity of an annulus of an atrioventricular valve, at least a portion of the sleeve that contains a distal end of the deployment manipulator; and deploying at least one anchor from the distal end of the deployment manipulator through a wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying includes deploying the at least one anchor while the angle is between 75 and 90 degrees.

In an embodiment, the deployment manipulator includes steering functionality, and placing the sleeve includes steering the deployment manipulator using the steering functionality.

Typically, the annuloplasty ring includes a partial annuloplasty ring, and positioning the anchor deployment manipulator includes positioning the anchor deployment manipulator at least partially within the lumen of the partial annuloplasty ring.

For some applications, the point on the wall is a first point on the wall, and the angle is a first angle, the at least one anchor is a first anchor of a plurality of anchors that also includes a second anchor most recently deployed before the first anchor through a second point on the wall, and deploying the first anchor includes deploying the first anchor while the distal end of the deployment manipulator is positioned such that the central longitudinal axis forms a second angle of between 45 and 90 degrees with a line defined by the first point and the second point.

For some applications, deploying the anchor includes deploying the anchor from the distal end of the deployment manipulator such that a coupling element of the anchor enters the cardiac tissue in a direction parallel to the central longitudinal axis.

For some applications, the anchor is shaped so as to define a coupling head and a tissue coupling element, which is shaped so as to define a shape selected from the group consisting of: a helix, a spiral, and a screw shaft, and deploying the anchor includes screwing the tissue coupling element into the cardiac tissue.

In an embodiment, the method further includes tightening the annuloplasty ring by winding a flexible contracting member of the ring around a spool coupled to the ring.

For some applications, deploying the anchor includes deploying the anchor from the atrium into an upper region of a ventricular wall near the atrium.

For some applications, the deployment manipulator includes an anchor driver positioned within a sheath, the at least one anchor includes a plurality of anchors, and deploying the at least one anchor includes:

loading a first one of the anchors onto the anchor driver;

deploying the first one of the anchors through a wall of the sleeve and into the cardiac tissue;

withdrawing the anchor driver from the sheath and a body of the subject, while leaving the sheath lumen of the sleeve;

subsequently loading a second one of the anchors onto the anchor driver while the anchor driver is outside the body;

subsequently reintroducing the anchor driver into the body and the sheath; and subsequently deploying the second one of the anchors through the wall of the sleeve into the cardiac tissue.

For some applications, placing the at least a portion of the sleeve includes placing the at least a portion of the sleeve into a right atrium of the subject in a vicinity of a tricuspid valve. Alternatively, placing the at least a portion of the sleeve includes placing the at least a portion of the sleeve into a left atrium of the subject in a vicinity of the annulus of a mitral valve.

There is yet additionally provided, in accordance with an embodiment of the present invention, a method including:

positioning, during a transcatheter procedure, an anchor deployment manipulator at least partially in an atrium of a subject;

placing, into the atrium in a vicinity of an annulus of an atrioventricular valve, at least a portion of an annuloplasty ring; and coupling the annuloplasty ring to cardiac tissue by deploying at least one anchor from the deployment manipulator in the atrium and into an upper region of a ventricular wall near the atrium.

Typically, the atrioventricular valve is selected from the group consisting of: a mitral valve and a tricuspid valve.

In an embodiment, positioning the anchor deployment manipulator includes positioning at least a distal end of the deployment manipulator within a lumen of a sleeve of the annuloplasty ring, and coupling includes coupling the ring to the cardiac tissue by deploying the at least one anchor from the distal end of the deployment manipulator in the atrium, through a wall of the sleeve, and into the upper region of the ventricular wall. For some applications, deploying the anchor includes deploying the anchor into the upper region of the ventricular wall while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

For some applications, deploying the anchor includes deploying the anchor from the distal end of the deployment manipulator into the upper region of ventricular wall such that a coupling element of the anchor enters the ventricular wall in a direction parallel to a central longitudinal axis of the deployment manipulator through the distal end of the deployment manipulator.

There is also provided, in accordance with an embodiment of the present invention, apparatus including an annuloplasty system for use on a subject, the system including:

an annuloplasty ring, which includes a sleeve having a lumen;

at least one anchor;

an anchor deployment manipulator, which is configured to be removably positioned within the lumen of the sleeve, and which is configure to deploy the at least one anchor through a wall of the sleeve into cardiac tissue of the subject; and a pusher element which is positioned within the sleeve, and which is configured to, upon being pushed distally, move the distal end of the deployment manipulator proximally within the sleeve by engaging an interior surface of the sleeve.

In an embodiment, the deployment manipulator includes an outer tube that is shaped so as to define an opening that is within 3 mm of a distal end of the tube; and an anchor driver that is positioned at least partially within the outer tube, and which is configured to deploy the at least one anchor, and the pusher element is positioned such that a proximal portion thereof is within the outer tube, and a distal portion thereof extends out of the tube through the opening and into the lumen of the sleeve.

In an embodiment, the deployment manipulator includes an outer tube; and an anchor driver that is positioned at least partially within the outer tube, and which is configured to deploy the at least one anchor, and the pusher element is positioned outside of the outer tube.

For some applications, the pusher element is configured to, upon being pushed distally, move the distal end of the deployment manipulator proximally within the sleeve by engaging a distal end of the sleeve. Alternatively or additionally, the pusher element is configured to, upon being pushed distally, move the distal end of the deployment manipulator proximally within the sleeve by engaging the wall of the sleeve.

Typically, the annuloplasty ring includes a partial annuloplasty ring.

In an embodiment, the annuloplasty ring includes a spool coupled to the sleeve, and a flexible contracting member that is coupled to the spool and the sleeve, such that winding the contracting member around the spool tightens the ring.

There is further provided, in accordance with an embodiment of the present invention, a method including:

positioning an anchor deployment manipulator and a pusher element at least partially within a lumen of a sleeve of an annuloplasty ring;

placing, into an atrium of a subject in a vicinity of an annulus of an atrioventricular valve, at least a portion of the sleeve that contains a distal end of the deployment manipulator and a distal end of the pusher element;

moving the distal end of the deployment manipulator proximally within the sleeve by pushing the pusher element distally such that the pusher element engages an interior surface of the sleeve; and after moving the distal end of the deployment manipulator, deploying an anchor from the distal end of the deployment manipulator through a wall of the sleeve into cardiac tissue.

For some applications, the deployment manipulator includes an outer tube that is shaped so as to define an opening that is within 3 mm of a distal end of the tube, and positioning the pusher element at least partially within the lumen of the sleeve includes positioning the pusher element such that (a) a distal portion of the pusher element extends out of the tube through the opening and into the lumen of the sleeve, and (b) a proximal portion of the pusher element passes through the tube from the opening to a proximal end of the tube.

For some applications, the deployment manipulator includes an outer tube, and positioning the pusher element at least partially within the lumen of the sleeve includes positioning the pusher element outside of the outer tube.

For some applications, moving includes moving the distal end of the deployment manipulator by pushing the pusher element distally such that the pusher element engages a distal end of the sleeve. Alternatively or additionally, moving includes moving the distal end of the deployment manipulator by pushing the pusher element distally such that the pusher element engages the wall of the sleeve.

For some applications, moving the distal end of the deployment manipulator includes moving the distal end of the deployment manipulator a certain distance by pushing the pusher element the certain distance.

There is still further provided, in accordance with an embodiment of the present invention, apparatus including an annuloplasty ring for use on a subject, which includes:

a sleeve shaped so as to define a lumen therein that is open at a proximal end of the sleeve;

a contracting mechanism, coupled to the sleeve in a vicinity of a distal end of the sleeve; and an elongated contracting member, a first end of which is coupled to the contracting mechanism, and a second end of which is coupled to the sleeve in a vicinity of the proximal end of the sleeve, wherein the contracting mechanism includes a driving interface that is positioned so as to be accessible from within the lumen of the sleeve, and wherein the contracting mechanism is configured such that rotation of the driving interface shortens the ring by tightening the elongated contracting member.

Typically, the annuloplasty ring includes a partial annuloplasty ring.

For some applications, the apparatus further includes a screwdriver tool, which includes a head and a shaft, and the screwdriver tool is configured to be removably inserted partially into the lumen of the sleeve via the proximal end of the sleeve, such that the head is removably coupled from within the lumen to the driving interface of the contracting mechanism.

In an embodiment, the apparatus further includes at least one anchor; and an anchor deployment manipulator, configured to be removably positioned within the lumen of the sleeve, and, while so positioned, to deploy the anchor from a distal end of the deployment manipulator through a wall of the sleeve into cardiac tissue of the subject.

There is additionally provided, in accordance with an embodiment of the present invention, a method including:

coupling a sleeve of an annuloplasty ring to cardiac tissue of a subject at a plurality of sites in a vicinity of an annulus of an atrioventricular valve;

partially inserting a screwdriver tool into a lumen of the sleeve, the tool having a head and a shaft; and rotating the screwdriver tool such that the head, while within the lumen of the sleeve, shortens the ring by rotating a contracting mechanism of the ring that tightens an elongated contracting member coupled to the sleeve.

Typically, the annuloplasty ring includes a partial annuloplasty ring, and coupling includes coupling the sleeve of the partial annuloplasty ring to the cardiac tissue.

The present invention will be more fully understood from the following detailed description of embodiments thereof, taken together with the drawings, in which:

BRIEF DESCRIPTION OF THE DRAWINGS

FIG. 2 is a schematic longitudinal cross-sectional illustration of an anchor deployment manipulator, in accordance with an embodiment of the present invention;

FIG. 3 is a schematic longitudinal cross-sectional illustration of the anchor deployment manipulator of FIG. 2 advanced into the annuloplasty ring of FIG. 1A, in accordance with an embodiment of the present invention;

FIG. 4 is a schematic cross-sectional illustration of the anchor deployment manipulator of FIG. 2 advanced into the annuloplasty ring of FIG. 1A or 1B, taken along section IV-IV of FIG. 3, in accordance with an embodiment of the present invention;

FIGS. 5A-B are schematic illustrations of a screwdriver tool being used to rotate a spool of a contracting mechanism of the rings of FIGS. 1A and 1B, respective, in accordance with respective embodiments of the present invention;

FIG. 7 is a schematic illustration of the deployment of an anchor into cardiac tissue, in accordance with an embodiment of the present invention;

FIG. 8 is a schematic illustration of the system of FIGS. 1-4 comprising a flexible pusher element, in accordance with an embodiment of the present invention;

FIG. 9 is a schematic illustration of a pusher tube applied to a proximal end of the sleeve of FIGS. 1-4, in accordance with an embodiment of the present invention;

FIGS. 10 and 11 are schematic illustrations of the system of FIGS. 1-4 comprising a steerable tube, in accordance with respective embodiments of the present invention.

DETAILED DESCRIPTION OF EMBODIMENTS

Figure 1A:
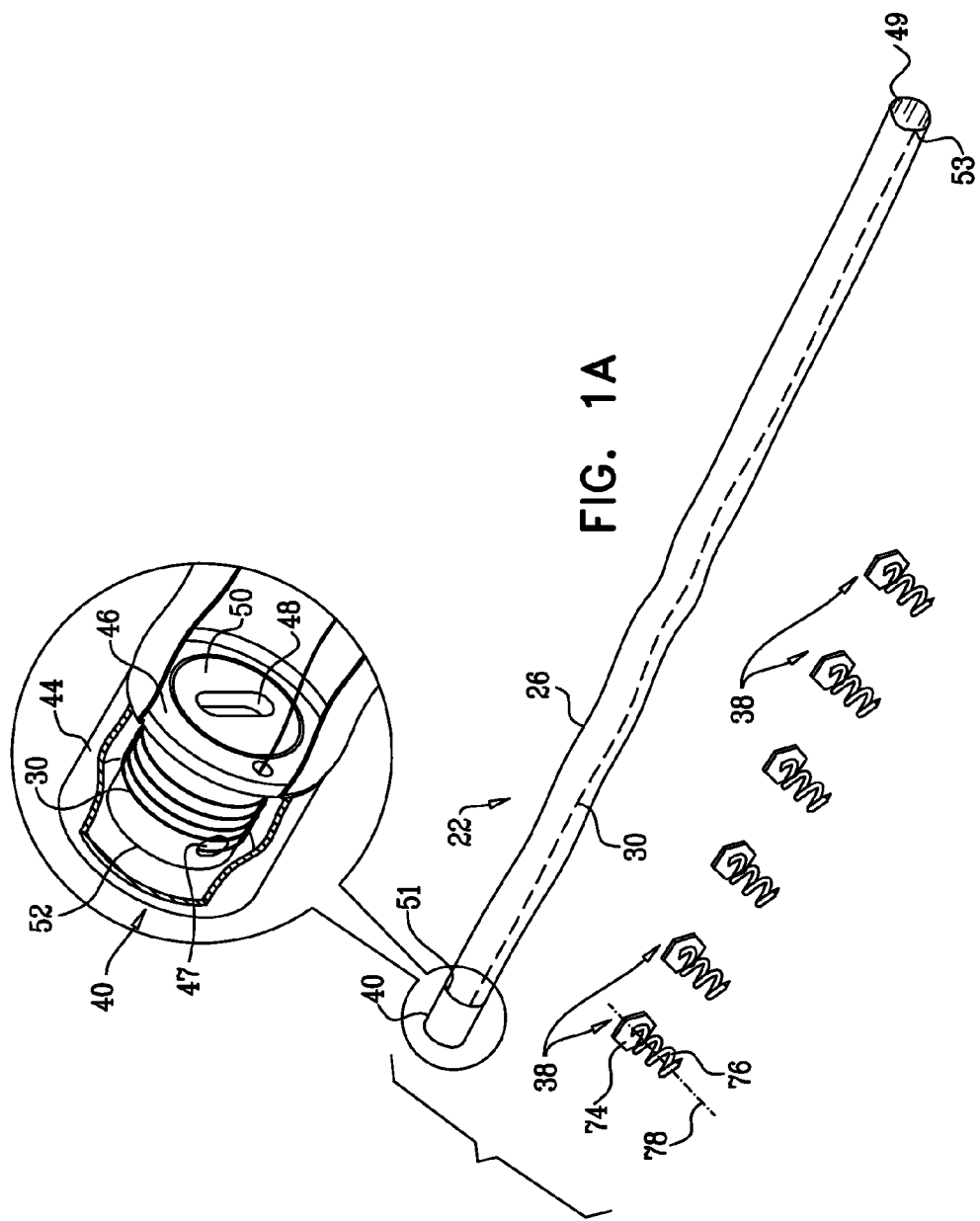
FIGS. 1A and 1B are schematic illustrations of an adjustable partial annuloplasty ring in a non-contracted state, in accordance with respective embodiments of the present invention.

FIGS. 1-4 are schematic illustrations of a system 20 for repairing a dilated atrioventricular valve, such as a mitral valve, in accordance with an embodiment of the present invention. System 20 comprises an adjustable partial annuloplasty ring 22, shown alone in FIGS. 1A and 1B in a non-contracted state, and an anchor deployment manipulator 24, shown alone in FIG. 2. Annuloplasty ring 22 comprises a flexible sleeve 26. Anchor deployment manipulator 24 is advanced into sleeve 26, as shown in FIGS. 3 and 4, and, from within the sleeve, deploys anchors 38 through a wall of the sleeve into cardiac tissue, thereby anchoring the ring around a portion of the valve annulus.

Figure 1B:
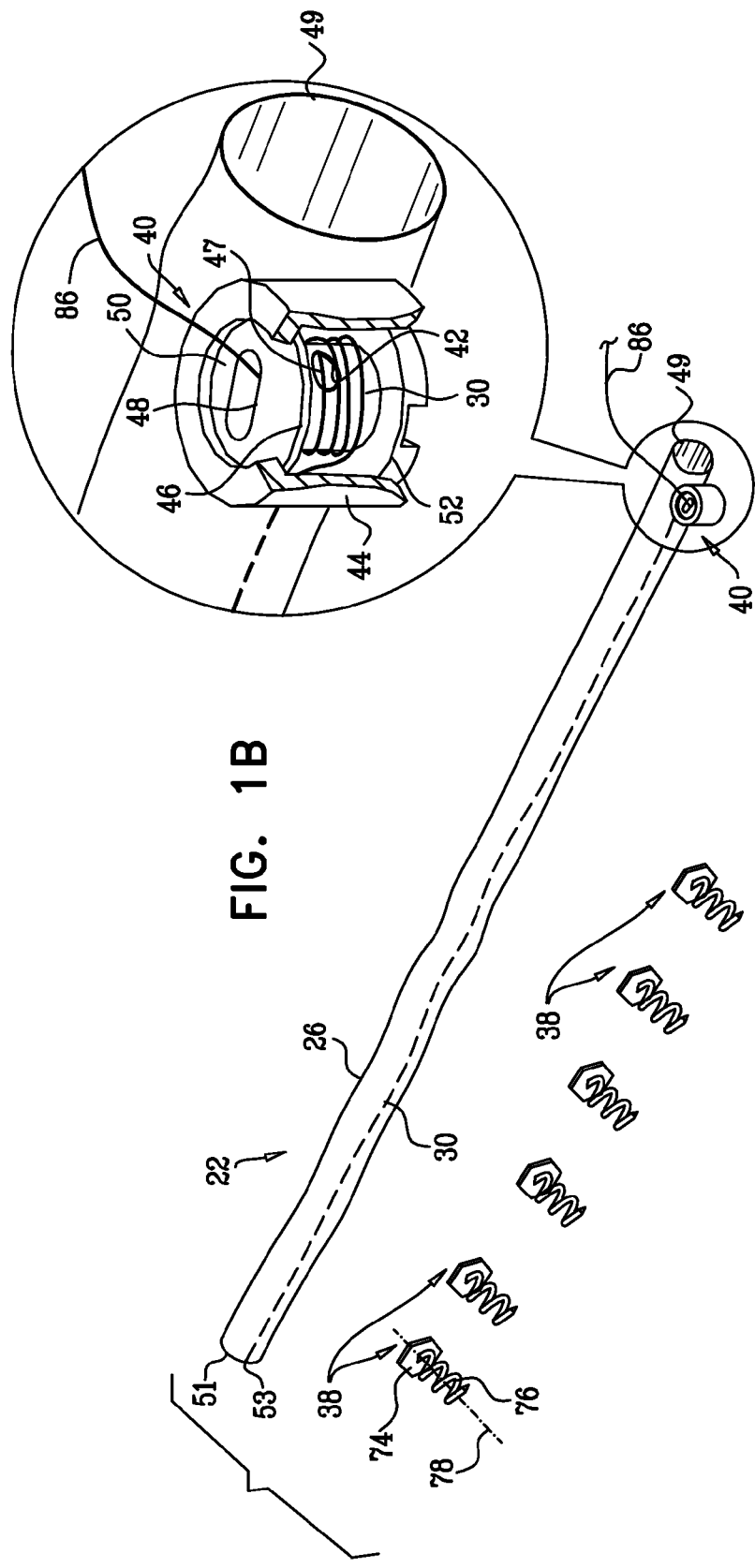

FIGS. 1A and 1B are schematic illustration of annuloplasty ring 22 in a non-contracted state, in accordance with respective embodiments of the present invention. Sleeve 26 is typically configured to be placed only partially around the valve annulus (i.e., to assume a C-shape), and, once anchored in place, to be contracted so as to circumferentially tighten the valve annulus. Alternatively, the ring is configured to be placed entirely around the valve annulus. In order to tighten the annulus, annuloplasty ring 22 comprises a flexible elongated contracting member 30 that extends along the ring.

Annuloplasty ring 22 further comprises a contracting mechanism 40, which facilitates contracting of the annuloplasty ring. Contracting mechanism 40 is described in more detail hereinbelow. In addition, the ring comprises a plurality of anchors 38, typically between about 5 and about 20 anchors, such as about 10 or about 16 anchors. In FIGS. 1A and 1B, anchors 38 are shown prior to their insertion into ring 22, while in FIG. 3 one of the anchors is shown deployed through the wall of sleeve 26, and a second one of the anchors is shown during deployment by anchor deployment manipulator 24. The insertion of the anchors into the sleeve and deployment of the anchors into cardiac tissue is described in detail hereinbelow.

Flexible sleeve 26 may comprise a braided, knitted, or woven mesh or a tubular structure comprising ePTFE. For some applications, the braid comprises metal and fabric fibers. The metal fibers, which may comprise Nitinol for example, may help define the shape of the sleeve, e.g., hold the sleeve open to provide space for passage and manipulation of deployment manipulator 24 within the sleeve. The fabric fibers may promote tissue growth into the braid. Optionally, the sleeve is somewhat elastic, which gives the sleeve a tendency to longitudinally contract, thereby helping tighten the sleeve. For example, the sleeve may be bellows- or accordion-shaped.

Typically, the sleeve is configured to have a tendency to assume a straight shape. This straightness helps the surgeon locate the next site for each subsequent anchor during the implantation procedure, as described hereinbelow with reference to FIGS. 6A-I. For example, because the sleeve assumes a generally straight shape, the sleeve may help provide an indication of distance between adjacent anchoring sites.

For some applications, the sleeve is configured to have a controllably variable stiffness. For example, a somewhat stiff wire may be placed in the sleeve to provide the stiffness, and subsequently be removed at the conclusion of the implantation procedure when the stiffness is no longer useful.

Elongated contracting member 30 comprises a wire, a ribbon, a rope, or a band, which typically comprises a flexible and/or superelastic material, e.g., nitinol, polyester, stainless steel, or cobalt chrome. In some embodiments, contracting member 30 comprises a braided polyester suture (e.g., Ticron). In some embodiments, contracting member 30 is coated with polytetrafluoroethylene (PTFE). In some embodiments, contracting member 30 comprises a plurality of wires that are intertwined to form a rope structure.

For some applications, contracting member 30 is positioned at least partially within a lumen of the sleeve 26, such as entirely within the lumen (as shown in FIGS. 1A-B, 5A-B, 6H, and 6I). For some applications in which the contracting member is positioned partially within the lumen, the contracting member is sewn into the wall of the sleeve, such that the contracting member is alternatingly inside and outside of the sleeve along the length of the sleeve (as shown in FIGS. 3, 8, and 9). Optionally, sleeve 26 defines an internal channel within which member 30 is positioned (configuration not shown). Alternatively, the contracting member is disposed outside the lumen of the sleeve, such as alongside an outer wall of the sleeve. For example, sleeve 26 may define an external channel within which member 30 is positioned, or the sleeve may comprise or be shaped so as to define external coupling elements, such as loops or rings (configuration not shown). For some applications, contracting member 30 is positioned approximately opposite the anchors.

In an embodiment of the present invention, contracting mechanism 40 comprises a housing 44 which houses a spool 46, i.e., a rotatable structure, to which a first end 47 of contracting member 30 is coupled. Spool 46 is positioned in a vicinity of (e.g., within 1 cm of) either a distal end 51 of sleeve 26, as shown in FIGS. 1A and 3, or a proximal end 49 of sleeve 26, as shown in FIG. 1B. A second end 53 of contracting member 30 is coupled to the sleeve in a vicinity of (e.g., within 1 cm of) the end of the sleeve opposite the end to which the spool is positioned. In the configuration shown in FIGS. 1A and 3, second end 53 of contracting member 30 is coupled to the sleeve in a vicinity of proximal end 49 of the sleeve, while in the configuration shown in FIG. 1B, the second end of the contracting member is coupled to the sleeve in a vicinity of distal end 51 of the sleeve. Rotation of spool 46 winds a portion of the contracting member around the spool, thereby pulling the far end of the ring toward the spool and shortening and tightening the ring.

Alternatively, in some configurations, spool 46 is positioned at an intermediary position along the sleeve, rather than in a vicinity of one of the ends. For these configurations, contracting member 30 comprises two contracting members, which are respectively connected to the two ends of the sleeve, and both of which are connected to the spool. Rotating the spool contracts both contracting members. These configuration may be implemented using techniques described in U.S. patent application Ser. No. 12/341,960 to Cabiri, which is incorporated herein by reference, with reference to FIG. 15 thereof.

Spool 46 is shaped to provide a hole 42 or other coupling mechanism for coupling first end 47 of contracting member 30 to the spool, and thereby to contracting mechanism 40. Spool 46 is shaped to define a driving interface 48. For some applications, driving interface 48 is female. For example, the interface may be shaped to define a channel which extends through the cylindrical portion of spool 46 from an opening provided by an upper surface 50 of spool 46 to an opening provided by a lower surface 52 of spool 46. Alternatively, driving interface 48 is shaped so as to define an indentation (e.g., a groove) that does not extend entirely through the cylindrical portion of the spool. Further alternatively, driving interface 48 is male, and defines a protrusion, e.g., a hexagonal head or a head having another shape.

A distal portion of a screwdriver tool 80, which is described hereinbelow with reference to FIGS. 5A-B, engages spool 46 via driving interface 48 and rotates spool 46 in response to a rotational force applied to the screwdriver. The rotational force applied to the screwdriver tool rotates spool 46 via the portion of the screwdriver tool that engages driving interface 48 of spool 46.

Spool 46 typically comprises a locking mechanism that prevents rotation of the spool after contracting member 30 has been tightened. For example, locking techniques may be used that are described with reference to FIG. 4 of above-mentioned U.S. application Ser. No. 12/341,960 to Cabiri.

Alternatively, in an embodiment of the present invention, contracting mechanism 40 is configured to tighten contracting member 30, crimp the contracting member to hold the contracting member taut, and subsequently cut the excess length of the contracting member.

FIG. 2 is a schematic longitudinal cross-sectional illustration of anchor deployment manipulator 24, FIG. 3 is a schematic longitudinal cross-sectional illustration of the anchor deployment manipulator advanced into annuloplasty ring 22, and FIG. 4 is a schematic cross-sectional illustration of the anchor deployment manipulator advanced into the annuloplasty ring, taken along section IV-IV of FIG. 3, in accordance with an embodiment of the present invention. Anchor deployment manipulator 24 is advanced into a lumen of sleeve 26, and, from within the lumen, deploys anchors 38 through a wall of the sleeve and into cardiac tissue, thereby anchoring the sleeve around a portion of the valve annulus. Typically, annuloplasty ring 22 and anchor deployment manipulator 24 are introduced into the heart via a sheath 104, as described hereinbelow with reference to FIGS. 6A-I.

In an embodiment of the present invention, at least one of anchors 38 is deployed from a distal end 60 of manipulator 24 while the distal end is positioned such that a central longitudinal axis 62 through distal end 60 of manipulator 24 forms an angle α (alpha) of between about 45 and 90 degrees with the wall of sleeve 26 at the point at which the anchor penetrates the wall, such as between about 75 and 90 degrees, e.g., about 90 degrees. (In FIG. 3, a line 64 schematically illustrates the plane tangential to the wall of the sleeve at the anchor-penetration point.) This anchor-penetration point is typically at a portion of the sleeve that extends distally beyond the distal end of outer tube 66 of deployment manipulator (which is described hereinbelow), i.e., that is no longer in contact with the outer surface of outer tube 66. Typically, all of the anchors are deployed at such angles, with the possible exception of the first anchor deployed near the distal end of the sleeve.

For some applications, at least one of anchors 38 is deployed from distal end 60 of manipulator 24 while distal end 60 is positioned such that longitudinal axis 62 through distal end 60 of manipulator 24 forms an angle β (beta) of between about 45 and 90 degrees (such as between about 75 and 90 degrees, e.g., about 90 degrees) with a line 65 defined by (a) a first point 67 at which the anchor currently being deployed penetrates the wall of the sleeve and (b) a second point 69 at which a most recently previously deployed anchor penetrates the wall of sleeve 26. Typically, all of the anchors are deployed at such angles, with the exception of the first anchor deployed near the distal end of the sleeve.

Typically, the anchors are deployed from distal end 60 of manipulator 24 into the cardiac tissue in a direction parallel to central longitudinal axis 62.

In an embodiment of the present invention, anchor deployment manipulator 24 comprises an outer tube 66 and an anchor driver 68 which is at least partially positioned within tube 66. Anchor driver 68 comprises an elongated, flexible shaft 70, having at its distal end a driver head 72. Rotation of the anchor driver screws the anchors into the cardiac tissue. Each of anchors 38 is shaped so as to define a coupling head 74 and a tissue coupling element 76. The anchors are typically rigid. Tissue coupling elements 76 may, for example, be helical or spiral in shape (e.g., having the shape of a corkscrew), as shown in the figures, may comprises screws, or may have other shapes. Coupling heads 74 may be either male (e.g., a hex or square protrusion) or female (e.g., a straight slot, a hex opening, a Phillips opening, or a Robertson opening). The use of helical anchors, which are screwed into the cardiac tissue, generally minimizes the force that needs to be applied during deployment of the anchors into the cardiac tissue. Alternatively, the anchors may comprise staples, clips, spring-loaded anchors, or other tissue anchors described in the references incorporated hereinabove in the Background section, or otherwise known in the art. For some applications, outer tube 66 of deployment manipulator 24 is steerable, as known in the catheter art, while for other applications, a separate steerable tube is provided, as described hereinbelow with reference to FIG. 10 or FIG. 11. To provide steering functionality to deployment manipulator, outer tube 66, steerable tube 300 (FIG. 10), or steerable tube 320 (FIG. 11), as the case may be, typically comprises one or more steering wires, the pulling and releasing of which cause deflection of the distal tip of the tube.

In an embodiment of the present invention, each of tissue coupling elements 76 is shaped so as to define a longitudinal axis 78 (shown in FIGS. 1A-B), and is configured to penetrate the cardiac tissue in a direction parallel to longitudinal axis 78. Deployment manipulator 24 is configured to deploy tissue coupling element 76 from distal end 60 of the manipulator through the wall of sleeve 26 in a direction parallel to longitudinal axis 78 and parallel to central longitudinal axis 62 through distal end 60 of deployment manipulator 24 (shown in FIGS. 2, 3, and 7-10).

For some applications, the plurality of anchors are applied using the manipulator by loading a first one of the anchors onto the anchor driver, and deploying the anchor into the cardiac tissue. The anchor driver is withdrawn from the subject's body (typically while leaving outer tube 66 of the deployment manipulator in place in the sleeve), and a second one of the anchors is loaded onto the anchor driver. The anchor driver is reintroduced into the outer tube of the manipulator, and the second anchor is deployed. These steps are repeated until all of the anchors have been deployed. Alternatively, the entire deployment manipulator, including the anchor driver, is removed from the body and subsequently reintroduced after being provided with another anchor. Further alternatively, the deployment manipulator is configured to simultaneously hold a plurality of anchors, and to deploy them one at a time (configuration not shown).

Typically, the first anchor 38 is deployed most distally in sleeve 26 (generally at or within a few millimeters of a distal end 51 of the sleeve), and each subsequent anchor is deployed more proximally, such that manipulator 24 is gradually withdrawn in a proximal direction during the anchoring procedure.

Figure 5B:
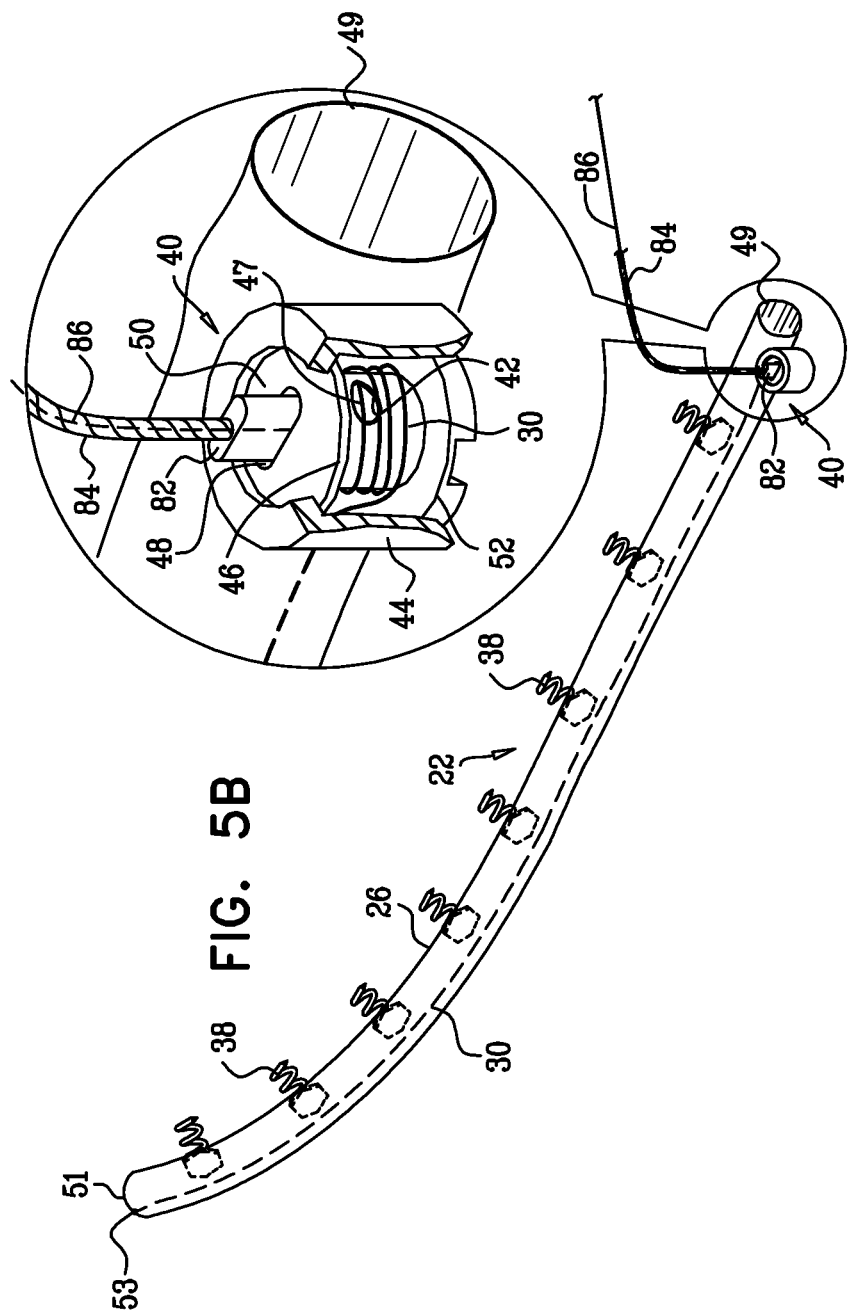

Reference is now made to FIGS. 5A-B, which are schematic illustrations of screwdriver tool 80 being used to rotate spool 46 of contracting mechanism 40 of ring 22, in accordance with respective embodiments of the present invention. Screwdriver tool 80 has a head 82 that is either male (e.g., comprising a screwdriver head, having, such as a slot-head, an Allen-head, a Phillips-head, a Robertson-head, or a hex-head) or female (e.g., comprising a wrench head, having, for example, a square or hex opening), as appropriate for the driving interface provided. Typically, the screwdriver tool comprises a shaft 84, at least a portion of which is flexible. For some applications, the screwdriver tool is used that is described in above-referenced U.S. patent application Ser. No. 12/341,960, with reference to FIG. 4 thereof. Alternatively, anchor driver 68 of deployment manipulator 24 serves as screwdriver tool 80, and is used to rotate the spool, in which case driving interface 48 is appropriately shaped to receive driver head 72 of anchor driver 68.

In the configuration shown in FIG. 5A, contracting member is coupled to distal end 51 of sleeve 26, as shown hereinabove in FIGS. 1A and 3. Contracting mechanism 40 is oriented such that driving interface 48 thereof is accessible from within sleeve 26. Screwdriver tool 80 is inserted into sleeve 26, and used to rotate spool 46 via the driving interface. Alternatively, anchor driver 68 of deployment manipulator 24 serves as screwdriver tool 80, and is used to rotate the spool, in which case driving interface 48 is appropriately shaped to engage driver head 72 of anchor driver 68. In either case, the sleeve thus serves to guide the screwdriver tool to driving interface 48. For some applications, an interior surface of the sleeve is tapered near the distal end of the sleeve, to help guide the screwdriver head to the driving interface. For some applications, during the implantation procedure, anchor deployment manipulator 24 is left slightly inserted into proximal end 49 of sleeve 26 after all of anchors 38 have been deployed, in order to facilitate passage of screwdriver tool 80 into sleeve 26.

In the configuration shown in FIG. 5B, access to driving interface 48 is provided from outside sleeve 26. For some applications, contracting mechanism 40 comprises a wire 86 that is attached to the mechanism and passes out of the body of the subject, typically via sheath 104. In order to readily bring the screwdriver tool to driving interface 48, screwdriver tool is guided over (as shown) the wire, or alongside the wire (configuration not shown).

For some applications, contracting mechanism 40 is positioned in a vicinity of (e.g., within 1 cm of) distal end 51 of sleeve 26, and access to driving interface 48 is provided from outside sleeve 26, as described with reference to FIG. 5B (in which the contracting mechanism is positioned in a vicinity of proximal end 49 of the sleeve).

For some applications in which access to driving interface 48 is provided from outside sleeve 26, the screwdriver tool is initially removably attached to the driving interface, prior to the commencement of the implantation procedure, and is subsequently decoupled from the driving interface after spool 46 has been rotated. In these applications, contracting mechanism 40 may be positioned in a vicinity of distal end 51 or proximal end 49 of sleeve 26, or at an intermediate location along the sleeve. Optionally, at least a portion of a shaft of the screwdriver tool is positioned within sheath 104, which is described hereinbelow with reference to FIGS. 6A-I.

Reference is now made to FIGS. 6A-I, which are schematic illustrations of a procedure for implanting annuloplasty ring 22 to repair a mitral valve 130, in accordance with an embodiment of the present invention. The procedure is typically performed with the aid of imaging, such as fluoroscopy, transesophageal echo, and/or echocardiography.

Figure 6A:
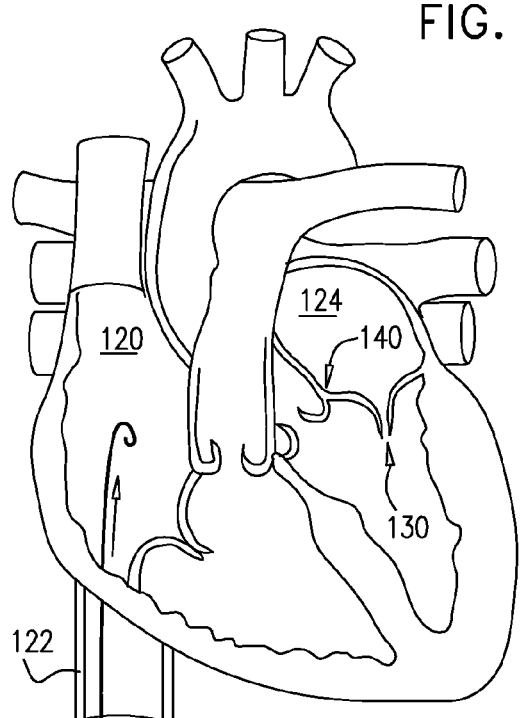
FIGS. 6A-I are schematic illustrations of a procedure for implanting the annuloplasty ring of FIG. 1A to repair a mitral valve, in accordance with an embodiment of the present invention.

The procedure typically begins by advancing a semi-rigid guidewire 102 into a right atrium 120 of the patient, as shown in FIG. 6A.

Figure 6B:
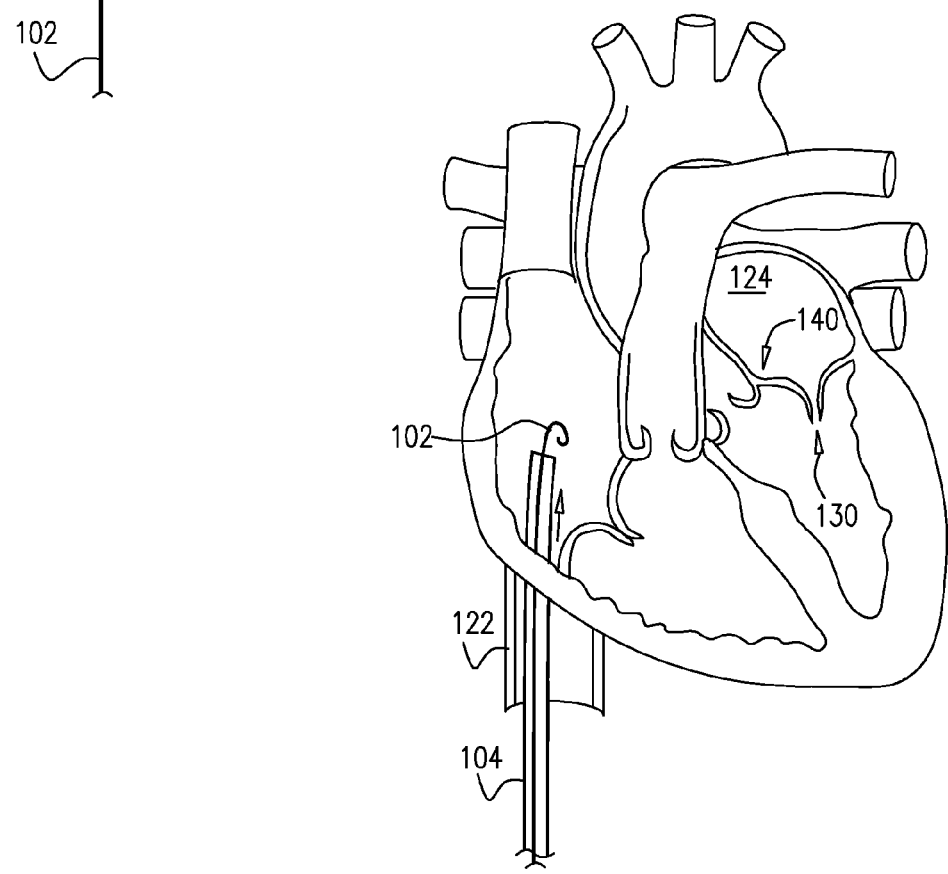
Figure 6C:
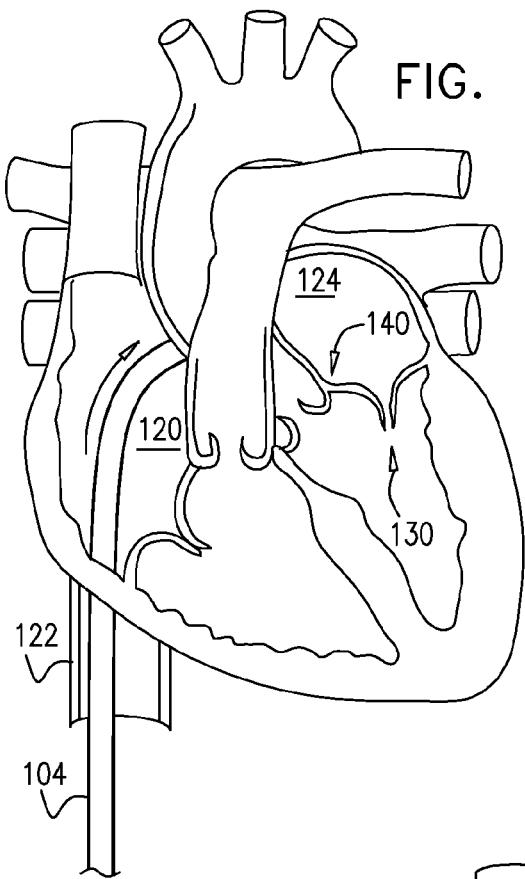

As show in FIG. 6B, guidewire 102 provides a guide for the subsequent advancement of a sheath 104 therealong and into the right atrium. Once sheath 104 has entered the right atrium, guidewire 102 is retracted from the patient's body. Sheath 104 typically comprises a 14-20 F sheath, although the size may be selected as appropriate for a given patient. Sheath 104 is advanced through vasculature into the right atrium using a suitable point of origin typically determined for a given patient. For example:

- sheath 104 may be introduced into the femoral vein of the patient, through an inferior vena cava 122, into right atrium 120, and into a left atrium 124 transseptally, typically through the fossa ovalis;
- sheath 104 may be introduced into the basilic vein, through the subclavian vein to the superior vena cava, into right atrium 120, and into left atrium 124 transseptally, typically through the fossa ovalis; or
- sheath 104 may be introduced into the external jugular vein, through the subclavian vein to the superior vena cava, into right atrium 120, and into left atrium 124 transseptally, typically through the fossa ovalis.

In an embodiment of the present invention, sheath 104 is advanced through an inferior vena cava 122 of the patient (as shown) and into right atrium 120 using a suitable point of origin typically determined for a given patient.

Sheath 104 is advanced distally until the sheath reaches the interatrial septum.

Figure 6D:
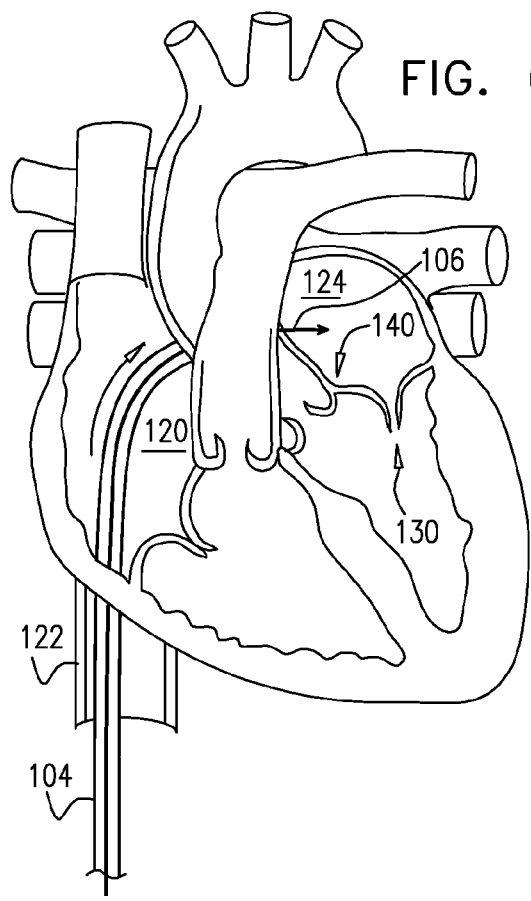

As shown in FIG. 6D, a resilient needle 106 and a dilator (not shown) are advanced through sheath 104 and into the heart. In order to advance sheath 104 transseptally into left atrium 124, the dilator is advanced to the septum, and needle 106 is pushed from within the dilator and is allowed to puncture the septum to create an opening that facilitates passage of the dilator and subsequently sheath 104 therethrough and into left atrium 124. The dilator is passed through the hole in the septum created by the needle. Typically, the dilator is shaped to define a hollow shaft for passage along needle 106, and the hollow shaft is shaped to define a tapered distal end. This tapered distal end is first advanced through the hole created by needle 106. The hole is enlarged when the gradually increasing diameter of the distal end of the dilator is pushed through the hole in the septum.

Figure 6E:
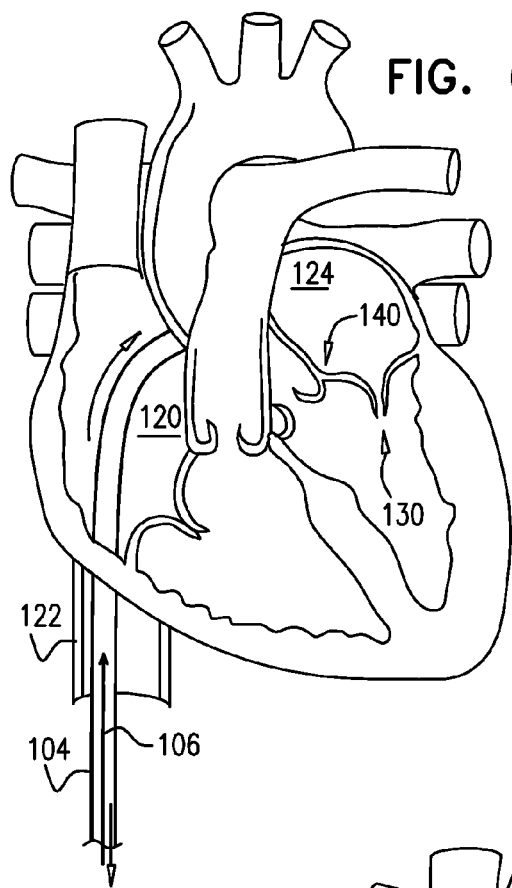

The advancement of sheath 104 through the septum and into the left atrium is followed by the extraction of the dilator and needle 106 from within sheath 104, as shown in FIG. 6E.

Figure 6F:
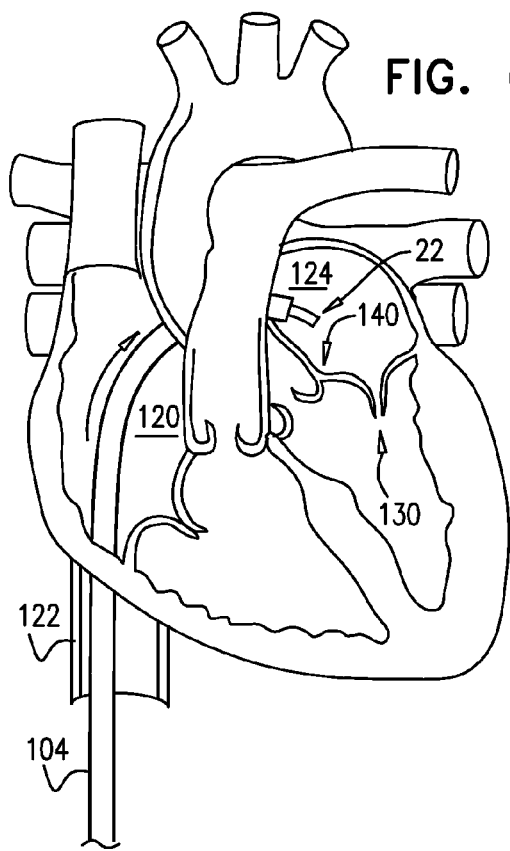

As shown in FIG. 6F, annuloplasty ring 22 (with anchor deployment manipulator 24 therein) is advanced through sheath 104 into left atrium 124.

Figure 6G:
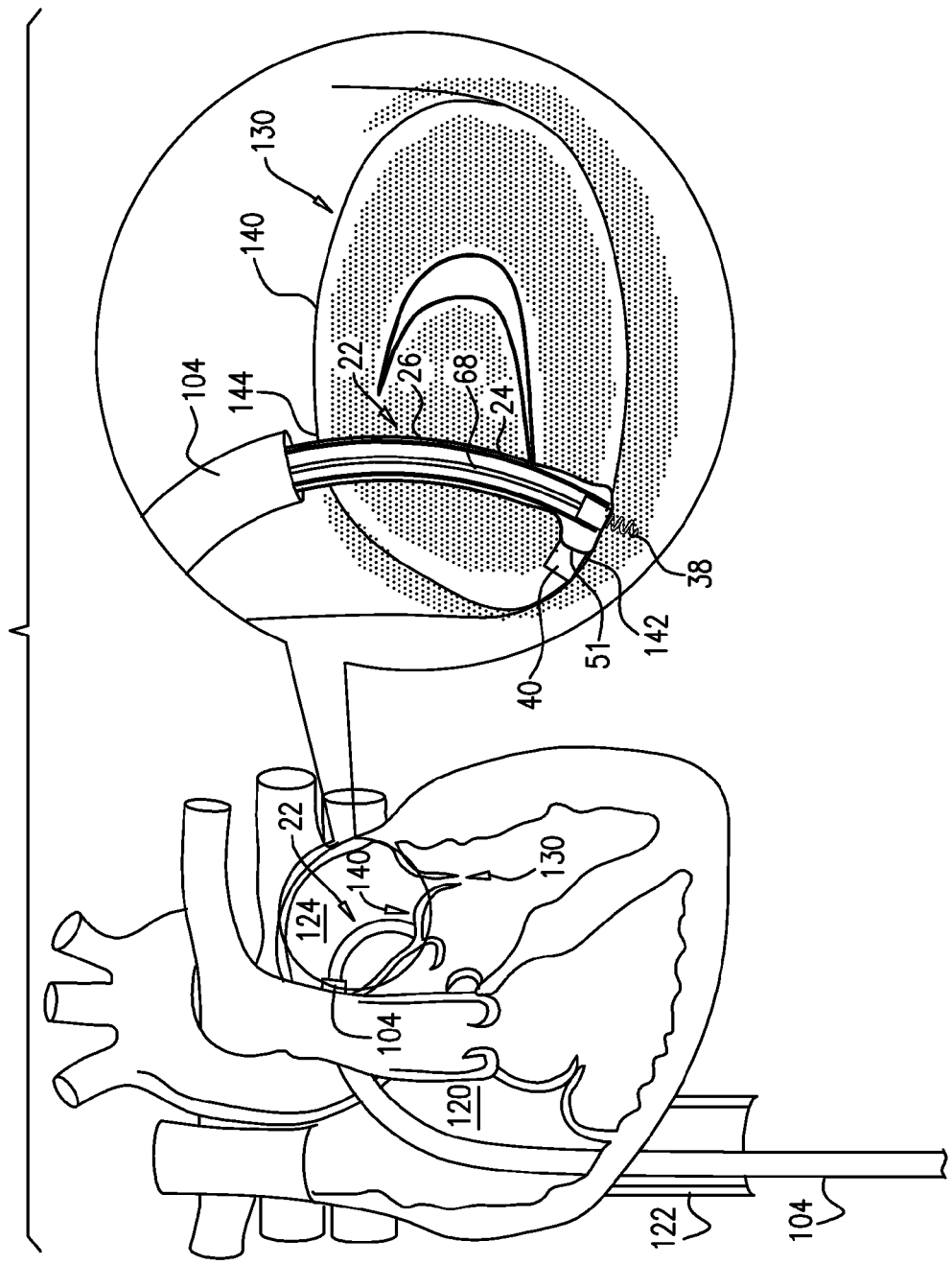

As shown in FIG. 6G, distal end 51 of sleeve 26 is positioned in a vicinity of a left fibrous trigone 142 of an annulus 140 of mitral valve 130. (It is noted that for clarity of illustration, distal end 51 of sleeve 26 is shown schematically in the cross-sectional view of the heart, although left trigone 142 is in reality not located in the shown cross-sectional plane, but rather out of the page closer to the viewer.) Alternatively, the tip is positioned in a vicinity of a right fibrous trigone 144 of the mitral valve (configuration not shown). Further alternatively, the distal tip of the sleeve is not positioned in the vicinity of either of the trigones, but is instead positioned elsewhere in a vicinity of the mitral valve, such as in a vicinity of the anterior or posterior commissure. For some applications, outer tube 66 of anchor deployment manipulator 24 is steerable, as is known in the catheter art, while for other applications, a separate steerable tube is provided, as described hereinbelow with reference to FIG. 10 and FIG. 11. In either case, the steering functionality typically allows the area near the distal end of the manipulator to be positioned with six degrees of freedom. Once positioned at the desired site near the selected trigone, manipulator 24 deploys a first anchor 38 through the wall of sleeve 26 into cardiac tissue near the trigone.

Figure 6H:
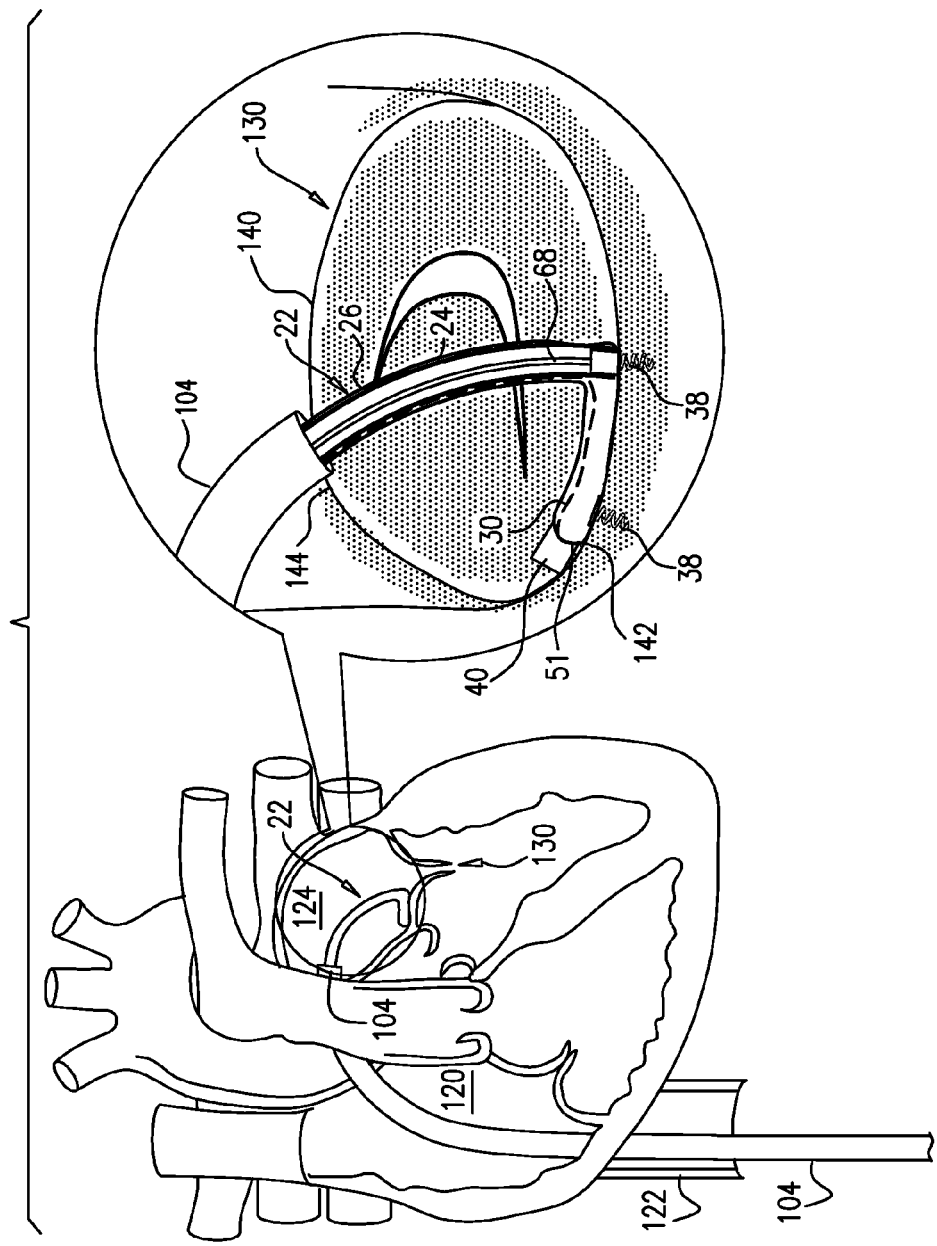

As shown in FIG. 6H, deployment manipulator 24 is repositioned along annulus 140 to another site selected for deployment of a second anchor 38. Typically, the first anchor is deployed most distally in the sleeve (generally at or within a few millimeters of the distal tip of the sleeve), and each subsequent anchor is deployed more proximally, such that the manipulator is gradually withdrawn in a proximal direction during the anchoring procedure. The already-deployed first anchor 38 holds the anchored end of sleeve 26 in place, so that the sleeve is drawn from the site of the first anchor towards the site of the second anchor. Deployment manipulator 24 deploys the second anchor through the wall of the sleeve into cardiac tissue at the second site. Depending on the tension applied between the first and second anchor sites, the portion of sleeve 26 therebetween may remain tubular in shape, or may become flattened, which may help reduce any interference of the ring with blood flow.

For some applications, in order to provide the second and subsequent anchors, anchor driver 68 is withdrawn from the subject's body via sheath 104 (typically while leaving outer tube 66 of the deployment manipulator in place in the sleeve), provided with an additional anchor, and then reintroduced into the subject's body and into the outer tube. Alternatively, the entire deployment manipulator, including the anchor driver, is removed from the body and subsequently reintroduced upon being provided with another anchor. Further alternatively, deployment manipulator 24 is configured to simultaneously hold a plurality of anchors, and to deploy them one at a time at the selected sites.

Figure 6I:
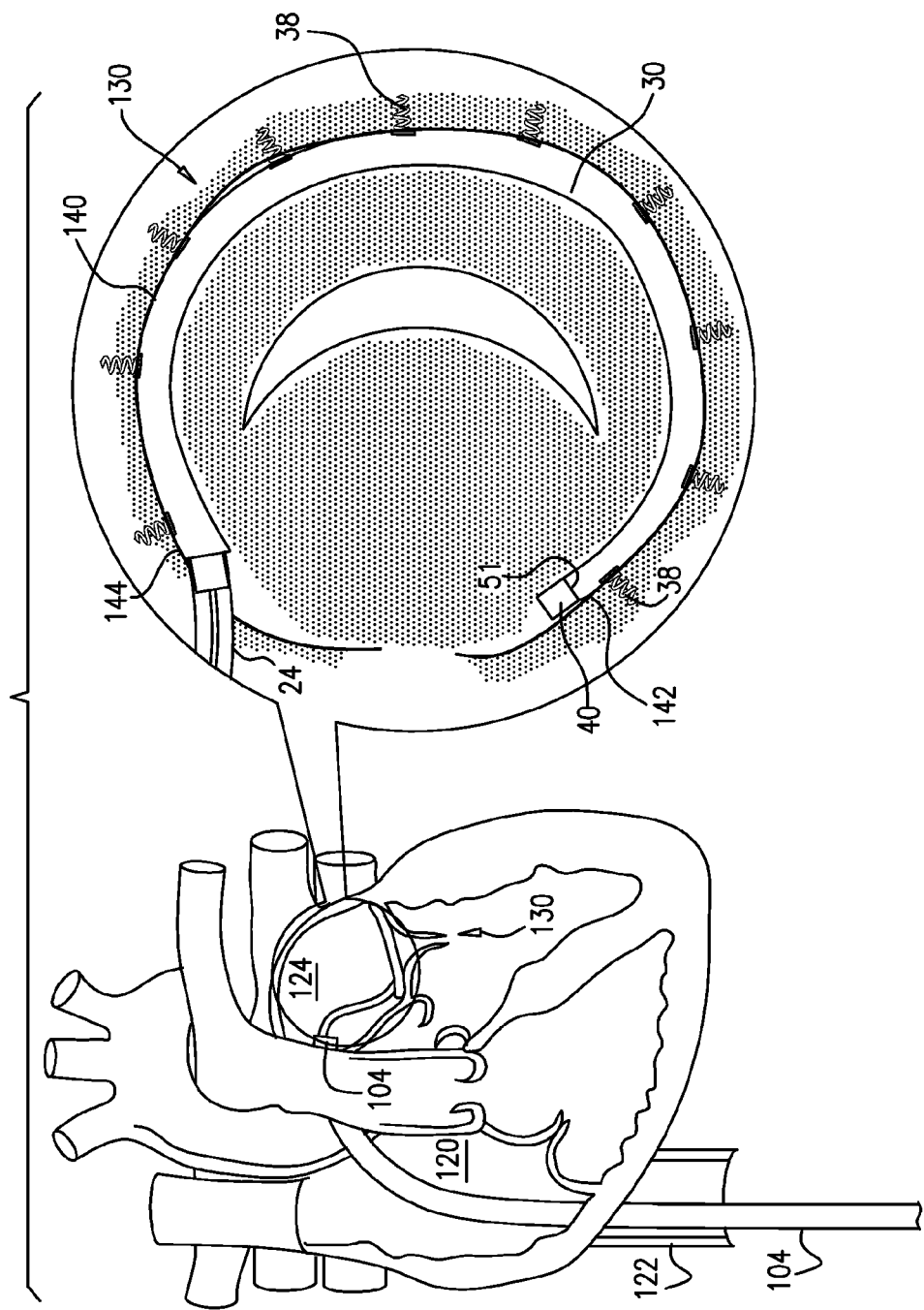

As shown in FIG. 6I, the deployment manipulator is repositioned along the annulus to additional sites, at which respective anchors are deployed, until the last anchor is deployed in a vicinity of right fibrous trigone 144 (or left fibrous trigone 142 if the anchoring began at the right trigone). Alternatively, the last anchor is not deployed in the vicinity of a trigone, but is instead deployed elsewhere in a vicinity of the mitral valve, such as in a vicinity of the anterior or posterior commissure.

As described hereinabove with reference to FIGS. 1A and 1B, a screwdriver tool or anchor driver 68 of deployment manipulator is used to rotate spool 46 of contracting mechanism 40, in order to tighten ring 22. (For clarity of illustration, contracting member 30 of ring 22, although provided, is not shown in FIGS. 6A-I.) Alternatively, another technique is used to tighten the ring, such as described hereinabove.

For some applications, sleeve 26 is filled with a material (e.g., polyester, polytetrafluoroethylene (PTFE), polyethylene terephthalate (PET), or expanded polytetrafluoroethylene (ePTFE)) after being implanted. The material is packed within at least a portion, e.g., 50%, 75%, or 100%, of the lumen of sleeve 26. The filler material functions to prevent (1) formation within the lumen of sleeve 26 of clots or (2) introduction of foreign material into the lumen which could obstruct the sliding movement of contracting member 30.

For some applications, proximal end 49 of sleeve 26 is closed upon completion of the implantation procedure. Alternatively, the proximal end of the sleeve may have a natural tendency to close when not held open by manipulator 24.

Reference is made to FIG. 7, which is a schematic illustration of the deployment of one of anchors 38 into cardiac tissue, in accordance with an embodiment of the present invention. In this embodiment, one or more (such as all) of anchors 38 are deployed from left atrium 124, through tissue of the atrial wall, and into tissue of an upper region of the ventricular wall 150 near the atrium. Because the tissue of the upper region of ventricular wall is thicker than that of the atrial wall, deploying the anchors into the upper region of the ventricular wall generally provides more secure anchoring. In addition, because the anchors are not deployed laterally through the atrial wall, the risk of perforating the atrial wall is reduced.

Annuloplasty ring 22 may be advanced toward annulus 140 in any suitable procedure, e.g., a transcatheter procedure, a minimally invasive procedure, or an open heart procedure (in which case one or more elements of system 20 are typically rigid). Regardless of the approach, the procedure typically includes the techniques described hereinabove with reference to FIGS. 6G-I and 7.

For some applications, following initial contraction of annuloplasty ring 22 during the implantation procedure, the ring may be further contracted or relaxed at a later time after the initial implantation. Using real-time monitoring, tactile feedback and optionally in combination with fluoroscopic imaging, a screwdriver tool or anchor driver 68 of deployment manipulator 24 is reintroduced into the heart and used to contract or relax annuloplasty ring 22.

Reference is now made to FIG. 8, which is a schematic illustration of system 10 comprising a flexible pusher element 200, in accordance with an embodiment of the present invention. Pusher element 200 aids with accurately positioning successive anchors 38 during an implantation procedure, such as described hereinabove with reference to FIGS. 6H and 6I. For some applications, pusher element 200 is positioned partially within tube 66 of deployment manipulator 24 such that a distal portion 204 of pusher element 200 extends distally out of tube 66, through an opening 206 in a vicinity of a distal end of the tube (e.g., that is within 3 mm of the distal end, such as within 2 mm of the distal end). A proximal portion 202 of pusher element 200 passes through outer tube 66 from opening 206 to the proximal end of tube 66. Opening 206 is provided either through a wall of the tube (as shown in FIG. 8), or through the distal end of the tube (configuration not shown). Alternatively, pusher element 200 is positioned within sleeve 26, but outside of tube 66 (configuration not shown). Typically, the pusher element is elongated, and is as least as long as sleeve 26.

Pusher element 200 helps move the distal end of deployment manipulator 24 from a first site of the annulus at which the manipulator has already deployed a first anchor (e.g., anchor 38A in FIG. 8) to a second site for deployment of a second anchor (e.g., anchor 38B), in a direction indicated schematically by an arrow 210. Pusher element 200 is pushed distally out of opening 206 of tube 66, so that a distal end 212 of pusher element 200 engages and pushes against an interior surface of sleeve 26, in a direction indicated schematically by an arrow 214. The interior surface of the sleeve may be distal end 51 of the sleeve (as shown), or the wall of the sleeve at a location between distal end 51 and opening 206 (not shown). As a result, the distal end of manipulator 24 moves in the opposite direction, i.e., as indicated by arrow 210, toward a subsequent anchoring site. The movement in the direction of arrow 210 is generally along a line or curve defined by the portion of pusher element 200 already extended between the anchors that have already been deployed.

For some applications, as manipulator 24 is positioned at successive deployment sites of the cardiac tissue, pusher element 200 is extended respective distances through opening 206, each of which distances is successively greater. For other applications, after manipulator 24 is positioned at each successive deployment site, the pusher element is pulled back in a proximal direction, and again extended a desired distance in a distal direction, such that the pusher element pushes again the wall of the sleeve (at a different location on the wall for each successive relocation of manipulator 24).

This technique thus aids in locating each subsequent anchoring site for manipulator 24. The pusher element may also help control the distance between adjacent anchoring sites, because they surgeon may push the pusher element a known distance after deploying each anchor.

Pusher element 200 typically comprises a strip, wire, ribbon, or band, and has a cross-section that is circular, elliptical, or rectangular. Pusher element 200 typically comprises a flexible and/or superelastic material, such as a metal such as nitinol, stainless steel, or cobalt chrome. Distal end 212 of pusher element 200 is dull, so that it does not penetrate sleeve 26. For example, the distal end may be folded back, as shown in FIG. 8.

FIG. 9 is a schematic illustration of a pusher tube 250 applied to proximal end 49 of sleeve 26, in accordance with an embodiment of the present invention. Pusher tube 250 pushes gently in a distal direction on proximal end 49 of sleeve 26. For example, if, during withdrawal of outer tube 66 in a proximal direction, the outer tube snags on the wall of sleeve 26 (which, as mentioned above, may comprise braided or woven fabric), such pushing may help free the snag. For some applications, the techniques of this embodiment are practiced in combination with those of the embodiment described hereinbelow with reference to FIG. 12. (Although in the embodiment described with reference to FIG. 9, system 10 typically comprises contracting member 30, for clarity of illustration the contracting member is not shown in the figure.)

FIG. 10 is a schematic illustration of system 10 comprising a steerable tube 300, in accordance with an embodiment of the present invention. In this embodiment, outer tube 66 of deployment manipulator 24 is not steerable. Instead, to provide steering functionality, deployment manipulator 24 comprises a separate steering tube 300, which is positioned around at least a portion of outer tube 66. Outer tube 66, because it does not provide this steering functionality, may have a smaller diameter than in the embodiment described hereinabove with reference to FIG. 3. Because outer tube 66 has a smaller diameter, sleeve 26 may also have a smaller diameter than in the embodiment described hereinabove with reference to FIG. 3. For some applications, the techniques of this embodiment are practiced in combination with those of the embodiment described hereinabove with reference to FIG. 9. (Although in the embodiment described with reference to FIG. 10, system 10 typically comprises contracting member 30, for clarity of illustration the contracting member is not shown in the figure.)

FIG. 11 is a schematic illustration of system 10 comprising a steerable tube 320, in accordance with an embodiment of the present invention. In this embodiment, outer tube 66 of deployment manipulator 24 is not steerable. Steering functionality is instead provided by separate steering tube 320, which is positioned around at least a portion of shaft 70 of anchor driver 68, and within outer tube 66. For some applications, the techniques of this embodiment are practiced in combination with those of the embodiment described hereinabove with reference to FIG. 9. (Although in the embodiment described with reference to FIG. 11, system 10 typically comprises contracting member 30, for clarity of illustration the contracting member is not shown in the figure.)

Figure 12:
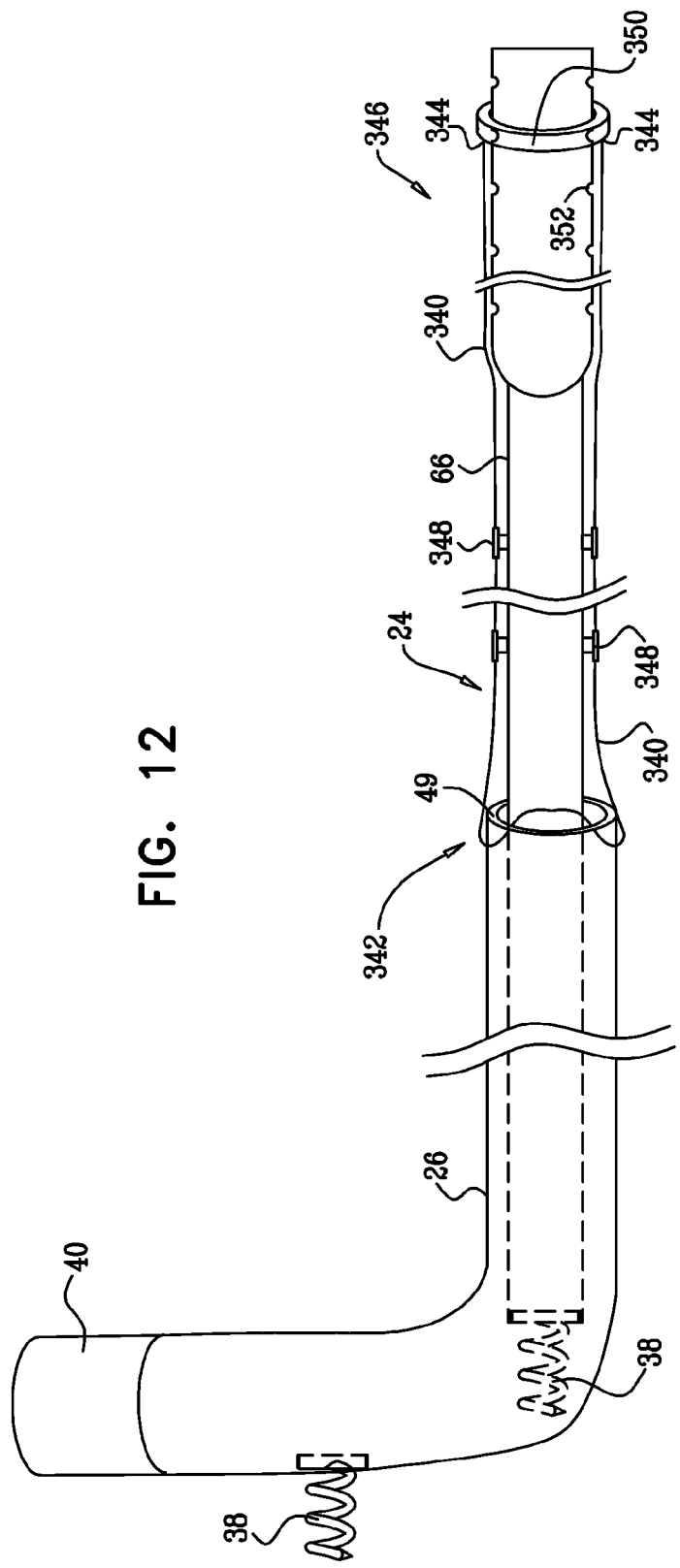
FIG. 12 is a schematic illustration of the system of FIGS. 1-4 comprising a pulling wire, in accordance with an embodiment of the present invention.

FIG. 12 is a schematic illustration of system 10 comprising a pulling wire 340, in accordance with an embodiment of the present invention. A distal portion 342 of pulling wire 340 is coupled to proximal end 49 of sleeve 26, such as by passing through one or more holes near the proximal end. One or more proximal portions 344 of the pulling wire are coupled to an external control handle 346 of system 10, which is manipulated by the surgeon outside of the subject's body. Optionally, a portion of deployment manipulator 24 (e.g., a portion of outer tube 66) which is never inserted in sleeve 26 comprises one or more coupling elements 348, such as loops or tubes, through which pulling wire 340 passes in order to hold the pulling wire close to the external surface of the deployment manipulator.

Pulling wire 340 holds sleeve 26 surrounding deployment manipulator 24. As the pulling wire is released in a distal direction as deployment manipulator 24 is withdrawn in a proximal direction, the release of the sleeve allows the sleeve to gradually be removed from around the deployment manipulator. In FIG. 12, the sleeve is shown partially removed from the manipulator, including the portion of the sleeve through which one of anchors 38 has been deployed.

For some applications, control handle 346 is configured to release pulling wire 340 incrementally, such that each time the wire is further released by a set distance. As a result, the deployment manipulator is withdrawn from the sleeve by this set distance, and subsequently-deployed anchors are approximately this set distance apart from one another. For example, the handle may comprise a control ring 350 that is coupled to proximal portions 344 of the wire, and removably engages slots 352 on the handle that are spaced apart by this set distance. Upon completion of the implantation procedure, in order to detach the pulling wire from the sleeve, one end of the wire may be cut or released, and the wire detached from the sleeve by pulling on the other end of the wire.

(Although in the embodiment described with reference to FIG. 12, system 10 typically comprises contracting member 30, for clarity of illustration the contracting member is not shown in the figure.)

Although annuloplasty ring 22 has been described hereinabove as comprising a partial annuloplasty ring, in some embodiments of the present invention, the ring instead comprises a full annuloplasty ring.

In some embodiments of the present invention, system 20 is used to treat an atrioventricular valve other than the mitral valve, i.e., the tricuspid valve. In these embodiments, annuloplasty ring 22 and other components of system 20 described hereinabove as being placed in the left atrium are instead placed in the right atrium. Although annuloplasty ring 22 is described hereinabove as being placed in an atrium, for some application the ring is instead placed in either the left or right ventricle.

For some applications, techniques described herein are practiced in combination with techniques described in one or more of the references cited in the Background section of the present patent application.

Additionally, the scope of the present invention includes embodiments described in the following applications, which are incorporated herein by reference. In an embodiment, techniques and apparatus described in one or more of the following applications are combined with techniques and apparatus described herein:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed on Feb. 16, 2007;

U.S. Provisional Patent Application 61/001,013 to Gross et al., entitled, "Segmented ring placement," filed Oct. 29, 2007;

PCT Patent Application PCT/IL07/001503 to Gross et al., entitled, "Segmented ring placement," filed on Dec. 5, 2007;

U.S. Provisional Patent Application 61/132,295 to Gross et al., entitled, "Annuloplasty devices and methods of delivery therefor," filed on Jun. 16, 2008;

U.S. patent application Ser. No. 12/341,960 to Cabiri, entitled, "Adjustable partial annuloplasty ring and mechanism therefor," filed on Dec. 22, 2008;

U.S. Provisional Patent Application to Miller et al., entitled, "Actively-engageable movement-restriction mechanism for use with an annuloplasty structure," filed on Feb. 1, 2009; and U.S. patent application Ser. No. 12/435,291 to Maisano et al., entitled, "Adjustable repair chords and spool mechanism therefor," filed on May 4, 2009.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an annuloplasty system for use on a subject, which comprises:

an annuloplasty ring, which comprises a sleeve having a wall defining a lumen that extends longitudinally along a length of the sleeve;

a contracting mechanism, coupled to the sleeve;

a contracting member that extends along at least a portion of the sleeve and is coupled at respective locations along the contracting member to (a) the contracting mechanism and (b) a portion of the sleeve, wherein the contracting mechanism is configured to contract the annuloplasty ring by pulling on the portion of the sleeve;

at least one anchor, shaped so as to define a tissue coupling element, which tissue coupling element is shaped so as to define a longitudinal axis, and is configured to penetrate cardiac tissue of the subject in a direction parallel to the longitudinal axis; and an anchor deployment manipulator, configured to be removably positioned within the lumen of the sleeve, and, while so positioned, to deploy the tissue coupling element from a distal end of the deployment manipulator by rotating the tissue coupling element in order to penetrate the tissue coupling element through the wall of the sleeve into the cardiac tissue in the direction parallel to the longitudinal axis of the tissue coupling element and parallel to a central longitudinal axis of the deployment manipulator through the distal end of the deployment manipulator.

2. The apparatus according to claim 1, wherein the annuloplasty ring has first and second longitudinally-opposed ends, and wherein the lumen extends longitudinally between the first and second ends.

3. The apparatus according to claim 2, wherein the annuloplasty ring comprises a partial annuloplasty ring.

4. The apparatus according to claim 2, wherein one of the first and the second ends of the annuloplasty ring is closed.

5. The apparatus according to claim 2, wherein a proximal end of the sleeve has a natural tendency to close when not held open by the anchor deployment manipulator.

6. The apparatus according to claim 1, wherein the coupling element is shaped so as to define a shape selected from the group consisting of: a helix, a spiral, and a screw shaft.

7. The apparatus according to claim 1, wherein the contracting mechanism comprises a spool, wherein the contracting member has a portion wound around the spool, and wherein the spool is arranged such that rotation of the spool contracts the annuloplasty ring by winding the contracting member around the spool.

8. The apparatus according to claim 1, wherein the deployment manipulator comprises steering functionality.

9. The apparatus according to claim 1,
wherein the apparatus further comprises a steerable tube, which is configured to provide steering functionality,
wherein the deployment manipulator further comprises (a) an outer tube and (b) an anchor driver, which is at least partially positioned within the outer tube and comprises an elongated, flexible shaft, and
wherein the outer tube is at least partially positioned within the steerable tube, such that a portion of the sleeve is radially between the outer tube and the steerable tube.

10. The apparatus according to claim 9, wherein the apparatus further comprises a sheath, through which the steerable tube, the sleeve, and the deployment manipulator are advanceable.

11. The apparatus according to claim 1, wherein the deployment manipulator is configured to deploy the at least one anchor from the distal end of the deployment manipulator through the wall of the sleeve into the cardiac tissue, while the distal end of the deployment manipulator is positioned such that the central longitudinal axis through the distal end of the deployment manipulator forms an angle of between 45 and 90 degrees with the wall of the sleeve at a point at which the anchor penetrates the wall.

12. The apparatus according to claim 11,
wherein the point on the wall is a first point on the wall, and the angle is a first angle,
wherein the at least one anchor is a first anchor of a plurality of anchors that also includes a second anchor most recently deployed before the first anchor through a second point on the wall, and
wherein the deployment manipulator is configured to deploy the first anchor while the distal end of the deployment manipulator is positioned such that the central longitudinal axis forms a second angle of between 45 and 90 degrees with a line defined by the first point and the second point.

13. The apparatus according to claim 1, further comprising a pusher element which is positioned within the sleeve, and which is configured to, upon being pushed distally, move the distal end of the deployment manipulator proximally within the sleeve by engaging an interior surface of the sleeve.

14. The apparatus according to claim 1, wherein the at least one anchor comprises at least first and second anchors, the first and the second anchors being shaped so as to define respective tissue coupling elements, which tissue coupling elements are shaped so as to define respective longitudinal axes, and are configured to penetrate cardiac tissue of the subject in directions parallel to the respective longitudinal axes, and wherein the deployment manipulator is configured to:
deploy, from within the lumen, the tissue coupling element of the first anchor from the distal end of the deployment manipulator through a first portion of the wall of the sleeve defining the lumen, by penetrating the tissue coupling element of the first anchor through the first portion of the wall of the sleeve, into a first portion of the cardiac tissue in the direction parallel to the longitudinal axis of the tissue coupling element and parallel to the central longitudinal axis of the deployment manipulator through the distal end of the deployment manipulator, and
subsequently to deploying the tissue coupling element of the first anchor, deploy, from within the lumen, the tissue coupling element of the second anchor from the distal end of the deployment manipulator through a second portion of the wall of the sleeve defining the lumen, by penetrating the tissue coupling element of the second anchor through the second portion of the wall of the sleeve, into a second portion of the cardiac tissue in the direction parallel to the longitudinal axis of the tissue coupling element and parallel to the central longitudinal axis of the deployment manipulator through the distal end of the deployment manipulator.

15. The apparatus according to claim 1, wherein the deployment manipulator is configured to be removably positioned within the lumen of the sleeve longitudinally along the length of the sleeve, and, while so positioned, to deploy the tissue coupling element from the distal end of the deployment manipulator.

16. The apparatus according to claim 1, wherein the at least one anchor is shaped so as to define a coupling head and the tissue coupling element.

17. The apparatus according to claim 1, wherein the anchor deployment manipulator comprises an outer tube that is sized to fit snugly within the lumen of the sleeve.

18. A method comprising:
positioning an anchor deployment manipulator at least partially within a lumen of a sleeve of an annuloplasty ring, the sleeve having a wall shaped to define the lumen, and the lumen extending longitudinally along a length of the sleeve, wherein the annuloplasty ring includes a contracting mechanism, coupled to the sleeve, and a contracting member that extends along at least a portion of the sleeve and is coupled at a respective locations along the contracting member to (a) the contracting mechanism and (b) a portion of the sleeve;
placing, into an atrium of a subject in a vicinity of an annulus of an atrioventricular valve, at least a portion of the sleeve that contains a distal end of the deployment manipulator; and deploying at least one anchor from the distal end of the deployment manipulator, by rotating a tissue coupling element of the anchor in order to penetrate the tissue coupling element through the wall of the sleeve such that the tissue coupling element of the anchor enters cardiac tissue of the subject in a direction parallel to a central longitudinal axis of the deployment manipulator through the distal end of the deployment manipulator,
wherein the tissue coupling element is shaped so as to define a longitudinal axis, and wherein deploying the at least one anchor comprises deploying the at least one anchor from the distal end of the deployment manipulator through the wall of the sleeve, by penetrating the tissue coupling element through the wall of the sleeve, such that the tissue coupling element of the anchor enters cardiac tissue of the subject in a direction parallel to the longitudinal axis of the tissue coupling element, and
further comprising contracting the annuloplasty ring by actuating the contracting mechanism to pull on the portion of the sleeve.

19. The method according to claim 18, wherein deploying comprises deploying the at least one anchor from the distal end of the deployment manipulator through the wall of the sleeve into the cardiac tissue, while the distal end of the deployment manipulator is positioned such that the central longitudinal axis through the distal end of the deployment manipulator forms an angle of between 45 and 90 degrees with the wall of the sleeve at a point at which the anchor penetrates the wall.

20. The method according to claim 19,
wherein the point on the wall is a first point on the wall, and the angle is a first angle,
wherein the at least one anchor is a first anchor of a plurality of anchors that also includes a second anchor most recently deployed before the first anchor through a second point on the wall, and
wherein deploying the first anchor comprises deploying the first anchor while the distal end of the deployment manipulator is positioned such that the central longitudinal axis forms a second angle of between 45 and 90 degrees with a line defined by the first point and the second point.

21. The method according to claim 18, wherein the annuloplasty ring has first and second ends, wherein the lumen extends longitudinally between the first and second ends, wherein positioning the deployment manipulator comprises positioning the deployment manipulator within the lumen of the partial annuloplasty ring, and wherein the method further comprises advancing the deployment manipulator within the lumen between the first and second ends.

22. The method according to claim 18, wherein the deployment manipulator comprises steering functionality, and wherein placing the sleeve comprises steering the deployment manipulator using the steering functionality.

23. The method according to claim 18, wherein deploying the anchor comprises deploying the anchor from the atrium into an upper region of a ventricular wall near the atrium.

24. The method according to claim 18, further comprising:
positioning a pusher element at least partially within the lumen of the sleeve of the annuloplasty ring; and
moving the distal end of the deployment manipulator proximally within the sleeve by pushing the pusher element distally such that the pusher element engages an interior surface of the sleeve.

25. The method according to claim 18, wherein the contracting mechanism includes a spool, and wherein contracting the annuloplasty ring comprises contracting the annuloplasty ring by winding the contracting member around the spool.

26. The method according to claim 18, wherein:
deploying the at least one anchor comprises deploying a first anchor through a first portion of the wall of the sleeve by penetrating a tissue coupling element of the first anchor through the first portion of the wall of the sleeve from within the lumen, such that the tissue coupling element of the first anchor enters a first portion of cardiac tissue, and
the method further comprises, subsequently to deploying the first anchor through the first portion of the wall of the sleeve, deploying a second anchor from the distal end of the deployment manipulator through a second portion of the wall of the sleeve, by penetrating a tissue coupling element of the second anchor through the second portion of the wall of the sleeve from within the lumen, such that the tissue coupling element of the second anchor enters a second portion of cardiac tissue of the subject in the direction parallel to the central longitudinal axis of the deployment manipulator through the distal end of the deployment manipulator.

27. The apparatus according to claim 10,
wherein the apparatus further comprises a steerable tube, which is configured to provide steering functionality,
wherein the deployment manipulator further comprises (a) an outer tube and (b) an anchor driver, which is at least partially positioned within the outer tube and comprises an elongated, flexible shaft, and
wherein the outer tube is at least partially positioned within the steerable tube, such that a portion of the sleeve is radially between the outer tube and the steerable tube.

28. The apparatus according to claim 27, wherein the apparatus further comprises a sheath, through which the steerable tube, the sleeve, and the deployment manipulator are advanceable.

29. The method according to claim 18,
wherein placing the at least a portion of the sleeve in the vicinity of the annulus comprises steering the deployment manipulator using a steerable tube, which is configured to provide steering functionality,
wherein deploying the at least one anchor comprises deploying the at least one anchor using an anchor driver of the deployment manipulator, which anchor driver includes an elongated, flexible shaft which is at least partially positioned within an outer tube of the deployment manipulator, and
wherein the outer tube is at least partially positioned within the steerable tube, such that a portion of the sleeve is radially between the outer tube and the steerable tube.

30. The method according to claim 29, wherein placing the at least a portion of the sleeve comprises advancing the steerable tube, the sleeve, and the deployment manipulator through a sheath into the atrium.

31. Apparatus comprising an annuloplasty system for use on a subject, which comprises:
an annuloplasty ring, which comprises a sleeve having a wall defining a lumen that extends longitudinally along a length of the sleeve;
a contracting mechanism, coupled to the sleeve;
a contracting member that extends along at least a portion of the sleeve and is coupled at respective locations along the contracting member to (a) the contracting mechanism and (b) a portion of the sleeve, wherein the contracting mechanism is configured to contract the annuloplasty ring by pulling on the portion of the sleeve;

at least one anchor; and
an anchor deployment manipulator configured to be removably positioned within the lumen of the sleeve, and, while so positioned, to deploy the at least one anchor from a distal end of the deployment manipulator by rotating a tissue coupling element of the anchor in order to penetrate the tissue coupling element through the wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall.

32. The apparatus according to claim 31, wherein the annuloplasty ring has first and second longitudinally-opposed ends, and wherein the lumen extends longitudinally between the first and second ends.

33. The apparatus according to claim 32, wherein the annuloplasty ring comprises a partial annuloplasty ring.

34. The apparatus according to claim 32, wherein one of the first and the second ends of the annuloplasty ring is closed.

35. The apparatus according to claim 32, wherein a proximal end of the sleeve has a natural tendency to close when not held open by the anchor deployment manipulator.

36. The apparatus according to claim 31, wherein the deployment manipulator comprises steering functionality.

37. The apparatus according to claim 31,
wherein the point on the wall is a first point on the wall, and the angle is a first angle,
wherein the at least one anchor is a first anchor of a plurality of anchors that also includes a second anchor most recently deployed before the first anchor through a second point on the wall, and
wherein the anchor deployment manipulator is configured to deploy the first anchor while the distal end of the deployment manipulator is positioned such that the central longitudinal axis forms a second angle of between 45 and 90 degrees with a line defined by the first point and the second point.

38. The apparatus according to claim 31, wherein the anchor is shaped so as to define a tissue coupling element, which tissue coupling element is shaped so as to define a longitudinal axis, and is configured to penetrate cardiac tissue of the subject in a direction parallel to the longitudinal axis, and wherein the anchor deployment manipulator is configured to deploy the anchor from the distal end of the deployment manipulator such that the coupling element enters the cardiac tissue in a direction parallel to the central longitudinal axis of the deployment manipulator through the distal end of the deployment manipulator.

39. The apparatus according to claim 38, wherein the at least one anchor is shaped so as to define a coupling head and the tissue coupling element.

40. The apparatus according to claim 31, wherein the anchor is shaped so as to define a tissue coupling element, which is shaped so as to define a shape selected from the group consisting of: a helix, a spiral, and a screw shaft.

41. The apparatus according to claim 31, wherein the at least one anchor comprises at least first and second anchors, the first and the second anchors being shaped so as to define respective tissue coupling elements, which tissue coupling elements are shaped so as to define respective longitudinal axes, and are configured to penetrate cardiac tissue of the subject in directions parallel to the respective longitudinal axes, and wherein the deployment manipulator is configured to:

deploy, from within the lumen, the tissue coupling element of the first anchor from the distal end of the deployment manipulator through a first portion of the wall of the sleeve defining the lumen, by penetrating the tissue coupling element of the first anchor through the first portion of the wall of the sleeve, into a first portion of the cardiac tissue in the direction parallel to the longitudinal axis of the tissue coupling element and parallel to the central longitudinal axis of the deployment manipulator through the distal end of the deployment manipulator, and subsequently to deploying the tissue coupling element of the first anchor, deploy, from within the lumen, the tissue coupling element of the second anchor from the distal end of the deployment manipulator through a second portion of the wall of the sleeve defining the lumen, by penetrating the tissue coupling element of the second anchor through the second portion of the wall of the sleeve, into a second portion of the cardiac tissue in the direction parallel to the longitudinal axis of the tissue coupling element and parallel to the central longitudinal axis of the deployment manipulator through the distal end of the deployment manipulator.

42. The apparatus according to claim 31, wherein the deployment manipulator is configured to be removably positioned within the lumen of the sleeve longitudinally along the length of the sleeve, and, while so positioned, to deploy the tissue coupling element from the distal end of the deployment manipulator.

43. The apparatus according to claim 31, wherein the contracting mechanism comprises a spool, wherein the contracting member has a portion wound around the spool, and wherein the spool is arranged such that rotation of the spool contracts the annuloplasty ring by winding the contracting member around the spool.

44. The apparatus according to claim 31, wherein the anchor deployment manipulator comprises an outer tube that is sized to fit snugly within the lumen of the sleeve.

45. A method comprising:
positioning an anchor deployment manipulator at least partially within a lumen of a sleeve of an annuloplasty ring, the sleeve having a wall shaped to define the lumen, and the lumen extending longitudinally along a length of the sleeve, wherein the annuloplasty ring includes a contracting mechanism, coupled to the sleeve, and a contracting member that extends along at least a portion of the sleeve and is coupled at a respective locations along the contracting member to (a) the contracting mechanism and (b) a portion of the sleeve;

placing, into an atrium of a subject in a vicinity of an annulus of an atrioventricular valve, at least a portion of the sleeve that contains a distal end of the deployment manipulator;

deploying at least one anchor from the distal end of the deployment manipulator, by rotating a tissue coupling element of the anchor in order to penetrate the tissue coupling element through the wall of the sleeve into cardiac tissue of the subject, while the distal end of the deployment manipulator is positioned such that a central longitudinal axis of the deployment manipulator through the distal end of the deployment manipulator forms an angle of between 45 and 90 degrees with the wall of the sleeve at a point at which the anchor penetrates the wall; and contracting the annuloplasty ring by actuating the contracting mechanism to pull on the portion of the sleeve.

46. The method according to claim 45, wherein deploying comprises deploying the at least one anchor while the angle is between 75 and 90 degrees.

47. The method according to claim 45, wherein the deployment manipulator includes steering functionality, and wherein placing the sleeve comprises steering the deployment manipulator using the steering functionality.

48. The method according to claim 45, wherein the annuloplasty ring has first and second ends, wherein the lumen extends longitudinally between the first and second ends, wherein positioning the anchor deployment manipulator comprises positioning the anchor deployment manipulator at least partially within the lumen of the partial annuloplasty ring, and wherein the method further comprises advancing the deployment manipulator within the lumen between the first and second ends.

49. The method according to claim 45,
wherein the point on the wall is a first point on the wall, and the angle is a first angle,
wherein the at least one anchor is a first anchor of a plurality of anchors that also includes a second anchor most recently deployed before the first anchor through a second point on the wall, and
wherein deploying the first anchor comprises deploying the first anchor while the distal end of the deployment manipulator is positioned such that the central longitudinal axis forms a second angle of between 45 and 90 degrees with a line defined by the first point and the second point.

50. The method according to claim 45, wherein deploying the anchor comprises deploying the anchor from the distal end of the deployment manipulator such that a coupling element of the anchor enters the cardiac tissue in a direction parallel to the central longitudinal axis.

51. The method according to claim 45, wherein the anchor is shaped so as to define a tissue coupling element, which is shaped so as to define a shape selected from the group consisting of: a helix, a spiral, and a screw shaft, and wherein deploying the anchor comprises screwing the tissue coupling element into the cardiac tissue.

52. The method according to claim 45, wherein the contracting mechanism includes a spool, and wherein contracting the annuloplasty ring comprises contracting the annuloplasty ring by winding the contracting member around the spool.

53. The method according to claim 45, wherein deploying the anchor comprises deploying the anchor from the atrium into an upper region of a ventricular wall near the atrium.

54. The method according to claim 45,
wherein the deployment manipulator includes an anchor driver positioned within a sheath,
wherein the at least one anchor comprises a plurality of anchors, and
wherein deploying the at least one anchor comprises:
loading a first one of the anchors onto the anchor driver;
deploying the first one of the anchors through a wall of the sleeve and into the cardiac tissue;
withdrawing the anchor driver from the sheath and a body of the subject, while leaving the sheath lumen of the sleeve;
subsequently loading a second one of the anchors onto the anchor driver while the anchor driver is outside the body;
subsequently reintroducing the anchor driver into the body and the sheath; and
subsequently deploying the second one of the anchors through the wall of the sleeve into the cardiac tissue.

55. The method according to claim 45, wherein placing the at least a portion of the sleeve comprises placing the at least a portion of the sleeve into a right atrium of the subject in a vicinity of a tricuspid valve.

56. The method according to claim 45, wherein placing the at least a portion of the sleeve comprises placing the at least a portion of the sleeve into a left atrium of the subject in a vicinity of the annulus of a mitral valve.

57. The method according to claim 45, wherein:
deploying the at least one anchor comprises deploying a first anchor through a first portion of the wall of the sleeve by penetrating a tissue coupling element of the first anchor through the first portion of the wall of the sleeve from within the lumen, such that the tissue coupling element of the first anchor enters a first portion of cardiac tissue, and
the method further comprises, subsequently to deploying the first anchor through the first portion of the wall of the sleeve, deploying a second anchor from the distal end of the deployment manipulator through a second portion of the wall of the sleeve, by penetrating a tissue coupling element of the second anchor through the second portion of the wall of the sleeve from within the lumen, such that the tissue coupling element of the second anchor enters a second portion of cardiac tissue of the subject in the direction parallel to the central longitudinal axis of the deployment manipulator through the distal end of the deployment manipulator.

58. The method according to claim 45,
wherein placing the at least a portion of the sleeve in the vicinity of the annulus comprises steering the deployment manipulator using a steerable tube, which is configured to provide steering functionality,
wherein deploying the at least one anchor comprises deploying the at least one anchor using an anchor driver of the deployment manipulator, which anchor driver includes an elongated, flexible shaft which is at least partially positioned within an outer tube of the deployment manipulator, and
wherein the outer tube is at least partially positioned within the steerable tube, such that a portion of the sleeve is radially between the outer tube and the steerable tube.

59. The method according to claim 58, wherein placing the at least a portion of the sleeve comprises advancing the steerable tube, the sleeve, and the deployment manipulator through a sheath into the atrium.

* * * * *